(12) United States Patent
Cohen et al.

(10) Patent No.: US 9,330,237 B2
(45) Date of Patent: May 3, 2016

(54) PATTERN RECOGNITION AND FILTERING IN A THERAPY MANAGEMENT SYSTEM

(75) Inventors: Gary Cohen, Sherman Oaks, CA (US); Kristen Getschmann, Exeter, NH (US); Vidya Raman, Simi Valley, CA (US); Kenneth Ko, Monterey Park, CA (US); Biju Nair, Northridge, CA (US); Cary Talbot, Santa Clarita, CA (US); Tamir Nitzan, Woodland Hills, CA (US); Paul H. Kovelman, Simi Valley, CA (US); Bee Hess, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1419 days.

(21) Appl. No.: 12/343,875

(22) Filed: Dec. 24, 2008

(65) Prior Publication Data

US 2010/0161236 A1     Jun. 24, 2010

(51) Int. Cl.
| | | |
|---|---|---|
| G06F 19/00 | (2011.01) | |
| A61B 5/00 | (2006.01) | |
| A61M 5/172 | (2006.01) | |

(52) U.S. Cl.
CPC .......... *G06F 19/3443* (2013.01); *A61B 5/4836* (2013.01); *A61B 5/7275* (2013.01); *A61B 5/7282* (2013.01); *A61M 5/1723* (2013.01); *G06F 19/3456* (2013.01); *G06F 19/3468* (2013.01)

(58) Field of Classification Search
None
See application file for complete search history.

(56) References Cited

U.S. PATENT DOCUMENTS

| | | |
|---|---|---|
| 4,433,072 A | 2/1984 | Pusineri et al. |
| 4,494,950 A | 1/1985 | Fischell |
| 4,562,751 A | 1/1986 | Nason et al. |
| 4,671,288 A | 6/1987 | Gough |
| 4,678,408 A | 7/1987 | Nason et al. |

(Continued)

FOREIGN PATENT DOCUMENTS

| | | |
|---|---|---|
| EP | 1338295 | 8/2003 |
| WO | 9637246 A1 | 11/1996 |

(Continued)

OTHER PUBLICATIONS

Shichiri et al., "A Needle-Type Glucose Sensor—A Valuable Tool Not Only for a Self-Blood Glucose Monitoring But for a Wearable Artificial Pancreas-," Life Support Systems: The Journal of the European Society for Artificial Organs, Sep. 1984, vol. 2, supplement 1, pp. 7-9.

(Continued)

*Primary Examiner* — Bill Thomson
*Assistant Examiner* — Davin K Sands
(74) *Attorney, Agent, or Firm* — Medtronic MiniMed, Inc.

(57) ABSTRACT

A method of diabetes analysis includes receiving a plurality of glucose level readings for a user. A common event occurrence in at least two of the glucose level readings is determined. The at least two glucose level readings from the common event occurrence onwards in time for a time period is analyzed. A glucose level pattern formed by the at least two glucose level readings having a similar shape is determined. At least one anomalous glucose level reading having the similar shape and not conforming to the glucose level pattern is analyzed. The at least one anomalous glucose level reading is adapted to the pattern to form an adapted glucose level pattern. An insulin dosage for the time period beginning at the common event occurrence is calculated based on the adapted glucose level pattern.

14 Claims, 10 Drawing Sheets

(56) References Cited

U.S. PATENT DOCUMENTS

| | | |
|---|---|---|
| 4,685,903 A | 8/1987 | Cable et al. |
| 4,731,726 A | 3/1988 | Allen, III |
| 4,781,798 A | 11/1988 | Gough |
| 4,871,351 A | 10/1989 | Feingold |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,497,772 A | 3/1996 | Schulman et al. |
| 5,543,326 A | 8/1996 | Heller et al. |
| 5,544,649 A | 8/1996 | David et al. |
| 5,569,186 A | 10/1996 | Lord et al. |
| 5,582,593 A | 12/1996 | Hultman |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,750,926 A | 5/1998 | Schulman et al. |
| 5,779,665 A | 7/1998 | Mastrototaro et al. |
| 5,791,344 A | 8/1998 | Schulman et al. |
| 5,904,708 A | 5/1999 | Goedeke |
| 5,917,346 A | 6/1999 | Gord |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,249,705 B1 | 6/2001 | Snell |
| 6,259,937 B1 | 7/2001 | Schulman et al. |
| 6,329,161 B1 | 12/2001 | Heller et al. |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,554,798 B1 | 4/2003 | Mann et al. |
| 6,558,320 B1 | 5/2003 | Causey, III et al. |
| 6,560,741 B1 | 5/2003 | Gerety et al. |
| 6,564,104 B2 | 5/2003 | Nelson et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 7,399,277 B2 | 7/2008 | Saidara et al. |
| 7,547,281 B2 | 6/2009 | Hayes et al. |
| 2001/0023360 A1 | 9/2001 | Nelson et al. |
| 2002/0019586 A1 | 2/2002 | Teller et al. |
| 2002/0082665 A1 | 6/2002 | Haller et al. |
| 2002/0161288 A1 | 10/2002 | Shin et al. |
| 2002/0169636 A1 | 11/2002 | Eggers et al. |
| 2002/0181680 A1 | 12/2002 | Linder et al. |
| 2002/0193679 A1 | 12/2002 | Malave et al. |
| 2003/0023461 A1 | 1/2003 | Quintanilla et al. |
| 2003/0028082 A1 | 2/2003 | Thompson |
| 2003/0055406 A1 | 3/2003 | Lebel et al. |
| 2003/0060692 A1* | 3/2003 | Ruchti et al. ............ 600/310 |
| 2003/0078560 A1 | 4/2003 | Miller et al. |
| 2003/0088166 A1 | 5/2003 | Say et al. |
| 2003/0114836 A1 | 6/2003 | Estes et al. |
| 2003/0152823 A1 | 8/2003 | Heller |
| 2003/0160683 A1 | 8/2003 | Blomquist |
| 2003/0168338 A1 | 9/2003 | Gao et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1* | 11/2003 | Mault et al. ............ 600/316 |
| 2003/0212379 A1* | 11/2003 | Bylund et al. ............ 604/504 |
| 2003/0220552 A1 | 11/2003 | Reghabi et al. |
| 2004/0059201 A1* | 3/2004 | Ginsberg ............ 600/300 |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0068230 A1 | 4/2004 | Estes et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2004/0260478 A1 | 12/2004 | Schwamm |
| 2005/0038332 A1 | 2/2005 | Saidara et al. |
| 2005/0065464 A1 | 3/2005 | Talbot et al. |
| 2005/0113650 A1* | 5/2005 | Pacione et al. ............ 600/300 |
| 2005/0171513 A1 | 8/2005 | Mann et al. |
| 2005/0214585 A1 | 9/2005 | Li et al. |
| 2005/0240092 A1 | 10/2005 | Shah et al. |
| 2006/0010098 A1 | 1/2006 | Goodnow et al. |
| 2006/0036143 A1* | 2/2006 | Brister et al. ............ 600/345 |
| 2006/0173406 A1 | 8/2006 | Hayes et al. |
| 2006/0272652 A1 | 12/2006 | Stocker et al. |
| 2007/0016127 A1* | 1/2007 | Staib et al. ............ 604/66 |
| 2007/0016170 A1 | 1/2007 | Kovelman |
| 2007/0060870 A1 | 3/2007 | Tolle et al. |
| 2007/0106135 A1* | 5/2007 | Sloan et al. ............ 600/322 |
| 2007/0112298 A1* | 5/2007 | Mueller et al. ............ 604/65 |
| 2007/0142822 A1* | 6/2007 | Remde ............ 604/890.1 |
| 2007/0244383 A1 | 10/2007 | Talbot et al. |
| 2007/0276197 A1* | 11/2007 | Harmon ............ 600/300 |
| 2008/0033357 A1 | 2/2008 | Mann et al. |
| 2008/0064943 A1 | 3/2008 | Talbot et al. |
| 2008/0125700 A1 | 5/2008 | Moberg et al. |
| 2008/0125701 A1 | 5/2008 | Moberg et al. |
| 2008/0183060 A1* | 7/2008 | Steil et al. ............ 600/365 |
| 2008/0234943 A1* | 9/2008 | Ray et al. ............ 702/19 |
| 2009/0036753 A1* | 2/2009 | King ............ 600/301 |
| 2009/0112478 A1* | 4/2009 | Mueller et al. ............ 702/19 |

(56) References Cited

U.S. PATENT DOCUMENTS

| | | | | |
|---|---|---|---|---|
| 2009/0271729 | A1* | 10/2009 | Killoren Clark et al. | 715/771 |
| 2010/0125241 | A1* | 5/2010 | Prud'homme et al. | 604/65 |
| 2010/0145262 | A1* | 6/2010 | Bengtsson et al. | 604/66 |

FOREIGN PATENT DOCUMENTS

| | | | |
|---|---|---|---|
| WO | 0010628 A2 | 3/2000 | |
| WO | 0074753 A1 | 12/2000 | |
| WO | 02058537 A2 | 8/2002 | |
| WO | 02073503 A2 | 9/2002 | |
| WO | 02099600 A2 | 12/2002 | |
| WO | 03014735 A1 | 2/2003 | |
| WO | 2004009161 A1 | 1/2004 | |
| WO | 2005119524 A2 | 12/2005 | |
| WO | WO 2008052374 A1 * | 5/2008 | |

OTHER PUBLICATIONS

Shichiri et al., "An Artificial Endocrine Pancreas—Problems Awaiting Solution for Long-Term Clinical Applications of a Glucose Sensor," Frontiers Med. Biol. Engng., 1991, vol. 3, No. 4, pp. 283-292.
Shichiri et al., "Closed-Loop Glycemic Control with a Wearable Artificial Endocrine Pancreas Variations in Daily Insulin Requirements to Glycemic Response," Diabetes, Dec. 1984, vol. 33, pp. 1200-1202.
Shichiri et al., "Glycaemic Control in Pancreatectomized Dogs with a Wearable Artificial Endocrine Pancreas," Diabetologia, 1983, vol. 24, pp. 179-184.
Shichiri et al., "In Vivo Characteristics of Needle-Type Glucose Sensor—Measurements of Subcutaneous Glucose Concentrations in Human Volunteers-," Hormone and Metabolic Research, 1988, vol. 20, pp. 17-20.
Shichiri et al., "Membrane Design for Extending the Long-life of an Implantable Glucose Sensor," Diab. Nutr. Metab., 1989, vol. 2, pp. 309-313.
Shichiri et al., "Normalization of the Paradoxic Secretion of Glucagon in Diabetics Who Were Controlled by the Artificial Beta Cell," Diabetes, Apr. 1979, vol. 28, pp. 272-275.
Shichiri et al., "Telemetry Glucose Monitoring Device with Needle-Type Glucose Sensor: A Useful Tool for Blood Glucose Monitoring in Diabetic Individuals," Diabetes Care, May-Jun. 1986, vol. 9, No. 3, pp. 298-301.
Shichiri et al., "The Wearable Artificial Endocrine Pancreas with a Needle-Type Glucose Sensor: Perfect Glycemic Control in Ambulatory Diabetics," Acta Paediatr Jpn, 1984, vol. 26, pp. 359-370.
Shichiri et al., "Wearable Artificial Endocrine Pancreas with Needle-Type Glucose Sensor," The Lancet, Nov. 1982, pp. 1129-1131.
Shinkai et al., "Molecular Recognition of Mono- and Di-saccharides by Phenylboronic Acids in Solvent Extraction and as a Monolayer," J. Chem. Soc., 1991, pp. 1039-1041.
Shults et al., "A Telemetry-Instrumentation System for Monitoring Multiple Subcutaneously Implanted Glucose Sensors," IEEE Transactions on Biomedical Engineering, Oct. 1994, vol. 41, No. 10, pp. 937-942.
Sternberg et al., "Study and Development of Multilayer Needle-Type Enzyme-Based Glucose Microsensors," Biosensors, 1988, vol. 4, pp. 27-40.
Tamiya et al., "Micro Glucose Sensors Using Electron Mediators Immobilized on a Polypyrrole-Modified Electrode," Sensors and Actuators, 1989, vol. 18, pp. 297-307.
Tsukagoshi et al., "Specific Complexation with Mono- and Disaccharides That Can Be Detected by Circular Dichroism," J. Org. Chem., 1991, vol. 56, pp. 4089-4091.
Urban et al., "Miniaturized Multi-Enzyme Biosensors Integrated with pH Sensors on Flexible Polymer Carriers for In Vivo Applications," Biosensors & Bioelectronics, 1992, vol. 7, pp. 733-739.
Urban et al., "Miniaturized Thin-Film Biosensors Using Covalently Immobilized Glucose Oxidase," 1991, vol. 6, pp. 555-562.

Velho et al., "In Vivo Calibration of a Subcutaneous Glucose Sensor for Determination of Subcutaneous Glucose Kinetics," Diab. Nutr. Metab., 1988, vol. 3, pp. 227-233.
Wang et al., "Needle-Type Dual Microsensor for the Simultaneous Monitoring of Glucose and Insulin," Anal. Chem., Feb. 2001, vol. 73, No. 4, pp. 844-847.
Yamasaki et al., "Direct Measurement of Whole Blood Glucose by a Needle-Type Sensor," Clinica Chimica Acta, 1989, vol. 93, pp. 93-98.
Yokoyama, "Integrated Biosensor for Glucose and Galactose," Analytica Chimica Acta, 1989, vol. 218, pp. 137-142.
PCT Search Report and Written Opinion for PCT/US2006/044050.
International Preliminary Report on Patentability for PCT/US2006/044050.
PCT Search Report and Written Opinion for PCT/US2005/024311.
International Preliminary Report on Patentability for PCT/US2005/024311.
PCT Search Report and Written Opinion for PCT/US2006/021225.
International Preliminary Report on Patentability for PCT/US2006/021225.
PCT Search Report and Written Opinion for PCT/US2007/021662.
International Preliminary Report on Patentability for PCT/US2007/021662.
PCT Search Report and Written Opinion for PCT/US2008/006035. XP002456414, 3 pages.
Extended European Search Report dated May 14, 2007 for EP Application No. 06022507.5.
Walsh, John, P.A., C.D.E., "Changes in Diabetes Care a History of Insulin & Pumps Past, Present, and Future", Presentation, Sep. 2004.
Abel et al., "Experience with an Implantable Glucose Sensor as a Prerequisite of an Aritificial Beta Cell," Biomed. Biochim. Acta 43, 1984, pp. 577-584.
Bindra et al., "Design and in Vitro Studies of a Needle-Type Glucose Sensor for Subcutaneous Monitoring," Anal. Chem., Sep. 1991, vol. 63, No. 17, pp. 1692-1696.
Boguslavsky et al., "Applications of Redox Polymers in Biosensors," Solid State Ionics, 1993, vol. 60, pp. 189-197.
Geise et al., "Electropolymerized 1,3-diaminobenzene for the Construction of a 1,1'-dimethylferrocene Mediated Glucose Biosensor," Analytica Chimica Acta, 1993, vol. 281, pp. 467-473.
Gernet et al., "A Planar Glucose Enzyme Electrode," Sensors and Actuators, 1989, vol. 17, pp. 537-540.
Gernet et al., "Fabrication and Characterization of a Planar Electrochemical Cell and Its Application as a Glucose Sensor," Sensors and Actuators, 1989, vol. 18, pp. 59-70.
Gorton et al., "Amperometric Biosensors Based on an Apparent Direct Electron Transfer Between Electrodes and Immobilized Peroxidases," Analyst, Aug. 1992, vol. 117, pp. 1235-1241.
Gorton et al., "Amperometric Glucose Sensors Based on Immobilized Glucose-Oxidizing Enzymes and Chemically Modified Electrodes," Analytica Chimica Acta, 1991, vol. 249, pp. 43-54.
Gough et al., "Two-Dimensional Enzyme Electrode Sensor for Glucose," Analytical Chemistry, Oct. 1985, vol. 57, No. 12, pp. 2351-2357.
Gregg et al., "Cross-Linked Redox Gels Containing Glucose Oxidase for Amperometric Biosensor Applications," Anal. Chem., Feb. 1990, vol. 62, No. 3, pp. 258-263.
Gregg et al., "Redox Polymer Films Containing Enzymes," J. Phys. Chem., 1991, vol. 95, No. 15, pp. 5970-5975.
Hashiguchi et al., "Development of a Miniaturized Glucose Monitoring System by Combining a Needle-Type Glucose Sensor With Microdialysis Sampling Method," Diabetes Care, May 1994, vol. 17, No. 5, pp. 387-389.
Heller, "Electrical Wiring of Redox Enzymes," Accounts of Chemical Research, May 1990, vol. 23, No. 5, pp. 128-134.
Jobst et al., "Thin-Film Microbiosensors for Glucose-Lactate Monitoring," Analytical Chemistry, Sep. 1996, vol. 68, No. 18, pp. 3173-3179.
Johnson et al., "In vivo Evaluation of an Electroenzymatic Glucose Sensor Implanted in Subcutaneous Tissue," Biosensors & Bioelectronics, 1992, vol. 7, pp. 709-714.
Jonsson et al., "An Electrochemical Sensor for Hydrogen Peroxide Based on Peroxidase Adsorbed on a Spectrographic Graphite Electrode," Electroanalysis, 1989, vol. 1, pp. 465-468.

(56) References Cited

OTHER PUBLICATIONS

Kanapieniene et al., "Miniature Glucose Biosensor with Extended Linearity," Sensors and Actuators, 1992, vol. B, No. 10, pp. 37-40.

Kawamori et al., "Perfect Normalization of Excessive Glucagon Responses to Intravenous Arginine in Human Diabetes Mellitus with the Artficial Beta-Cell," Diabetes, Sep. 1980, vol, 29, pp. 762-765.

Kimura et al., "An Immobilized Enzyme Membrane Fabrication Method Using an Ink Jet Nozzle," Biosensors, 1988, vol. 4, pp. 41-52.

Koudelka et al., "In-vivo Behaviour of Hypodermically Implanted Microfabricated Glucose Sensors," Biosensors & Bioelectronics, 1991, vol. 6, pp. 31-36.

Koudelka et al., "Planar Amperometric Enzyme-Based Glucose Microelectrode," Sensors and Actuators, 1989, vol. 18, pp. 157-165.

Mastrototaro et al., "An Electroenzymatic Glucose Sensor Fabricated on a Flexible Substrate," Sensors and Actuators, 1991, vol. B, No. 5, pp. 139-144.

Mastrototaro et al., "An Electroenzymatic Sensor Capable of 72 Hour Continuous Monitoring of Subcutaneous Glucose," 14th International Diabetes Federation Congress, Jun. 1991, 19 pages.

McKean et al., "A Telemetry-Instrumentation System for Chronically Implanted Glucose and Oxygen Sensors," IEEE Transactions on Biomedical Engineering, Jul. 1988, vol. 35, No. 7, pp. 526-532.

Monroe, "Novel Implantable Glucose Sensors," ACL, Dec. 1989, pp. 8-16.

Morff et al., "Microfabrication of Reproducible, Economical, Electroenzymatic Glucose Sensors," Annual International Conference of the IEEE Engineering in Medicine and Biology Society, 1990, vol. 12, No. 2, pp. 483-484.

Moussy et al., "Performance of Subcutaneously Implanted Needle-Type Glucose Sensors Employing a Novel Trilayer Coating," Anal. Chem., 1993, vol. 65, pp. 2072-2077.

Nakamoto et al., "A Lift-Off Method for Patterning Enzyme-Immobilized Membranes in Multi-Biosensors," Sensors and Actuators, 1988, vol. 13, pp. 165-172.

Nishida et al., "Clinical Applications of the Wearable Artificial Endocrine Pancreas with the Newly Designed Needle-Type Glucose Sensor," Pathogenesis and Treatment of NIDDM, 1994, pp. 353-358.

Nishida et al., "Development of a Ferrocene-Mediated Needle-Type Glucose Sensor Covered with Newly Designed Biocompatible Membrane, 2-methacryloyloxyethyl phosphorylcholine-co-n-butyl methacrylate," Medical Progress Through Technology, 1995, vol. 21, pp. 91-103.

Poitout et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, 1993 vol. 36, pp. 658-663.

Reach, "A Method for Evaluating in vivo the Functional Characteristics of Glucose Sensors," Biosensors, 1986, vol. 2, pp. 211-220.

Shaw et al., "In vitro Testing of a Simply Constructed, Highly Stable Glucose Sensor Suitable for Implantation in Diabetic Patients," Biosensors & Bioelectronics, 1991, vol. 6, pp. 401-406.

\* cited by examiner

PATTERN RECOGNITION AND FILTERING IN A THERAPY MANAGEMENT SYSTEM

FIELD OF THE INVENTION

Embodiments of the present invention are directed to systems and methods for diabetes therapy management. Specifically, embodiments of the present invention are directed to applying pattern recognition and filtering algorithms to user medical information for analysis and managing diabetes.

BACKGROUND OF THE INVENTION

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source. Diabetes affects approximately eight percent of the total population in the United States alone.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue.

As of 1995, less than 5% of Type I diabetics in the United States were using infusion pump therapy. Presently, about 10% of the more than 1.5 million Type I diabetics in the U.S. are using infusion pump therapy. And the percentage of Type I diabetics that use an infusion pump is growing at an absolute rate of over 2% each year. Moreover, the number of Type I diabetics is growing at 3% or more per year. In addition, growing numbers of insulin-using Type II diabetics are also using infusion pumps. Physicians have recognized that continuous infusion provides greater control of a diabetic's condition, and are also increasingly prescribing it for patients. Although offering control, pump therapy can suffer from several complications that make use of traditional external infusion pumps less desirable for the user.

SUMMARY OF THE INVENTION

Embodiments of the present invention are directed to systems and methods of diabetes analysis. A plurality of glucose level readings for a user is received. A common event occurrence in at least two of the glucose level readings is determined. The at least two glucose level readings from the common event occurrence onwards in time for a time period is analyzed. A glucose level pattern formed by the at least two glucose level readings having a similar shape is determined. At least one anomalous glucose level reading having the similar shape and not conforming to the glucose level pattern is analyzed. The at least one anomalous glucose level reading is adapted to the pattern to form an adapted glucose level pattern. An insulin dosage for the time period beginning at the common event occurrence is calculated based on the adapted glucose level pattern. Embodiments of the present invention may perform these steps on a computer, or any other suitable system.

In particular embodiments, the glucose level readings are at least a portion of a 24-hour period. An average glucose level reading may be calculated from the adapted glucose level pattern, and the insulin dosage may be calculated based on the average glucose level reading. The common event occurrence may be, for example, breakfast, lunch, dinner, a meal bolus, a correction bolus, or a bedtime (to analyze an overnight period). The plurality of glucose level readings may represent glucose levels over time. The insulin dosage may be for a basal insulin dosage. The at least one anomalous glucose level reading having the similar shape may have at least one of: a greater or lesser magnitude, and a higher or lower basal glucose level than the at least two glucose level readings forming the glucose level pattern. The at least one anomalous glucose level reading having the similar shape may be compressed or stretched in time compared to the at least two glucose level readings forming the glucose level pattern. The at least one anomalous glucose level reading having the similar shape may occur differently from the common event occurrence of the at least two glucose level readings forming the glucose level pattern. Moreover, the glucose level readings may exclude those from the most recent days, especially if a user is learning a new behavior. Glucose level readings may be automatically or manually removed from analysis due to transient events in a user's life. Additionally, only those glucose level readings selected from days where the user has a periodic or transient condition (e.g., menstruation, illness, having a cold, being on a particular medication, stress and anxiety, etc.) may be selected for analysis.

Embodiments of the present invention are directed to systems and methods of diabetes analysis. Average glucose level information for a time period over a plurality of days is determined. A current event occurrence is determined. An event occurrence in the average glucose level information within the time period corresponding to the current event occurrence is determined, where the current event occurrence is at a different time of day than the event occurrence. The average glucose level information starting in time from the event occurrence within the time period is analyzed. A notification event in the average glucose level information starting in time from the event occurrence within the time period is determined. A current notification event in time from the current event occurrence based on a time span from the event occurrence to the notification event in the average glucose level information is predicted. An action is initiated in advance of the predicted current notification event. Embodiments of the present invention may perform these steps on a computer, or any other suitable system.

In particular embodiments, the current event occurrence and event occurrence may be, for example, breakfast, lunch, or dinner. The notification event may include, for example, hyperglycemia, hypoglycemia, a sharp glucose level spike, or a sharp glucose level drop. The action may include at least one of notifying a user of the predicted current notification event (which may utilize an auditory, visual, or vibrational alarm), recommending a bolus dosage to the user, automatically delivering a bolus of insulin, and automatically suspending delivery of insulin. The current event occurrence may be earlier or later than the event occurrence in the average glucose level information.

Embodiments of the present invention are directed to a method of providing bolus dosage recommendations for diabetics. A plurality of representative foods is presented to a user. The user's response to estimate a carbohydrate value for each one of the plurality of representative foods is received. An input is received from the user indicating a food to be consumed and an estimated carbohydrate value for the food to be consumed. A bolus dosage recommendation is calculated based on the input from the user and the user's response to estimate the carbohydrate value for at least one of the plurality of representative foods. Embodiments of the present invention may perform these steps on a computer, or any other suitable system.

In particular embodiments, the bolus dosage recommendation is increased if the user's response to estimate the carbohydrate value for the at least one of the plurality of representative foods corresponding to the food to be consumed is lower than a true carbohydrate value for the at least one of the plurality of representative foods corresponding to the food to be consumed, and the bolus dosage recommendation is decreased if the user's response to estimate the carbohydrate value for the at least one of the plurality of representative foods corresponding to the food to be consumed is higher than a true carbohydrate value for the at least one of the plurality of representative foods corresponding to the food to be consumed. The plurality of representative foods may include a plurality of food types, and the plurality of food types may include: grains, vegetables, fruits, dairy products, and meats.

DETAILED DESCRIPTION

Embodiments of the invention are described below with reference to flowchart and menu illustrations of methods, apparatus, and computer program products. It will be understood that each block of the flowchart illustrations, and combinations of blocks in the flowchart illustrations, can be implemented by computer program instructions (as can any menu screens described in the Figures). These computer program instructions may be loaded onto a computer or other programmable data processing apparatus to produce a machine, such that the instructions which execute on the computer (or other programmable data processing apparatus) create instructions for implementing the functions specified in the flowchart block or blocks. These computer program instructions may also be stored in a computer-readable memory that can direct a computer (or other programmable data processing apparatus) to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein.

Figure 1:
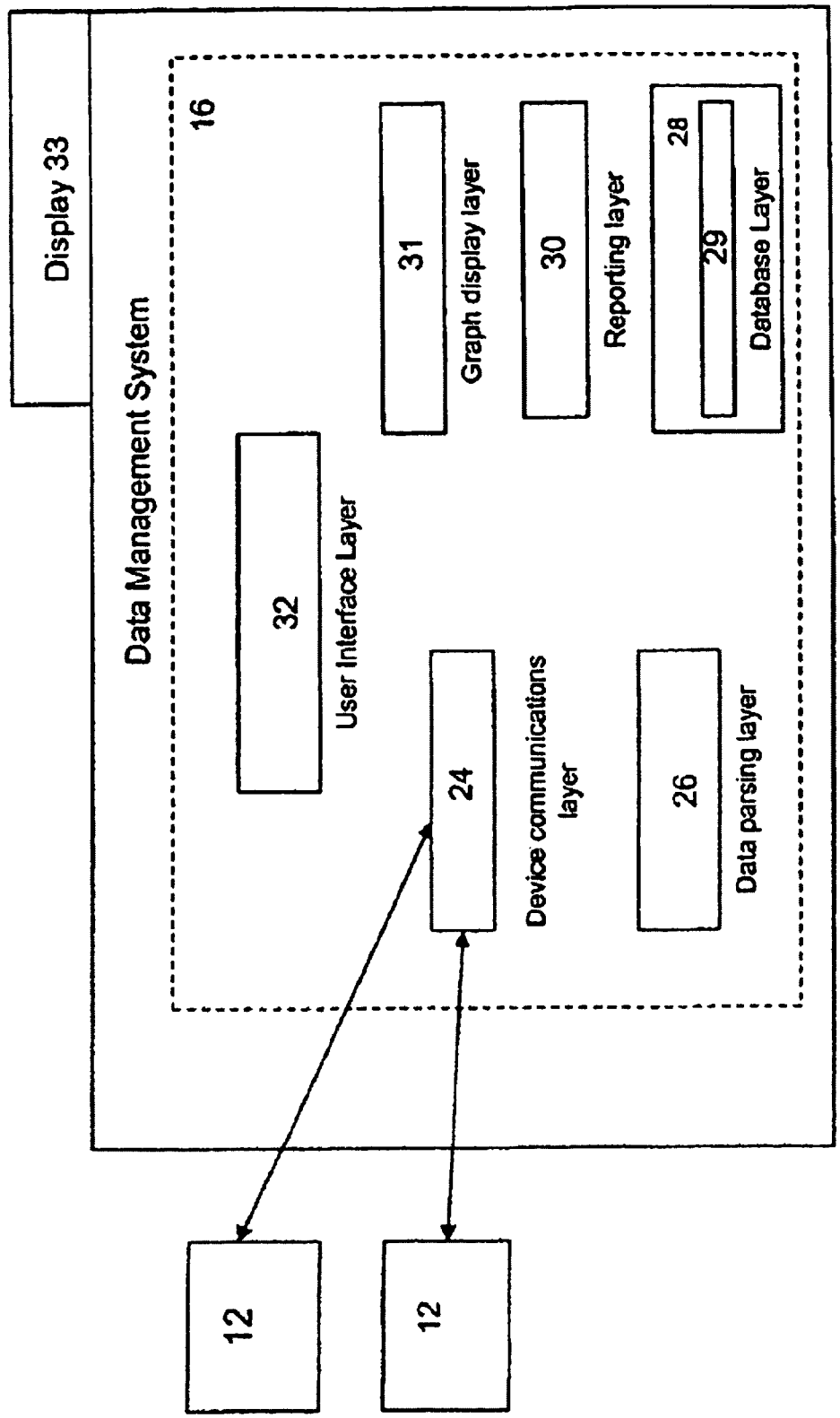
FIG. 1 illustrates a computing device including a display housing a diabetes data management system according to embodiments of the present invention.

FIG. 1 illustrates a computing device including a display housing a diabetes data management system according to embodiments of the present invention. The diabetes data management system (DDMS) may be referred to as the Medtronic MiniMed CARELINK™ system or as a medical data management system (MDMS) in some embodiments of the invention. The DDMS may be housed on a server or a plurality of servers which a user or a health care professional may access via a communications network via the Internet or the World Wide Web. This model of the DDMS, which is described as an MDMS is described in U.S. Pat. App. Pub. No. 2006/0031094, published Feb. 9, 2006, to Cohen et al., and is entitled, "Medical Data Management System and Process", which is herein incorporated by reference in its entirety.

While description of embodiments of the invention below are made in regard to monitoring medical or biological conditions for subjects having diabetes, the systems and processes below are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 100. The computing device 100 may be coupled to a display 33. In embodiments of the invention, the computing device 100 may be in a physical device separate from the display (such as in a personal computer, a mini-computer, etc.) In embodiments of the invention, the computing device 100 may be in a single physical enclosure or device with the display 33 such as a laptop where the display 33 is integrated into the computing device. In embodiments of the invention, the computing device 100 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 100 may also be a server located on the Internet that is accessible via a browser installed on a laptop computer, desktop computer, a network computer, or a PDA. The computing device 100 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 1, the data management system 16 comprises a group of interrelated software modules or layers that specialize in different tasks. The system software includes a device communication layer 24, a data parsing layer 26, a database layer 28, database storage devices 29, a reporting layer 30, a graph display layer 31, and a user interface layer 32. The diabetes data management system may communicate with a plurality of subject support devices 12, two of which are illustrated in FIG. 1. Although the different reference numerals refer to a number of layers, (e.g., a device communication layer, a data parsing layer, a database layer), each layer may include a single software module or a plurality of software modules. For example, the device communications layer 24 may include a number of interacting software modules, libraries, etc. In embodiments of the invention, the data management system 16 may be installed onto a non-volatile storage area (memory such as flash memory, hard disk, removable hard, DVD-RW, CD-RW) of the computing device 100. If the data management system 16 is selected or initiated, the system 16 may be loaded into a volatile storage (memory such as DRAM, SRAM, RAM, DDRAM) for execution.

The device communication layer 24 is responsible for interfacing with at least one, and, in further embodiments, to a plurality of different types of subject support devices 12, such as, for example, blood glucose meters, glucose sensors/monitors, or an infusion pump. In one embodiment, the device communication layer 24 may be configured to communicate with a single type of subject support device 12. However, in more comprehensive embodiments, the device communication layer 24 is configured to communicate with multiple different types of subject support devices 12, such as devices made from multiple different manufacturers, multiple different models from a particular manufacturer and/or multiple different devices that provide different functions (such as infusion functions, sensing functions, metering functions, communication functions, user interface functions, or combinations thereof). As described in more detail below, by providing an ability to interface with multiple different types of subject support devices 12, the diabetes data management system 16 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 24 allows the DDMS 16 to receive information from and transmit information to or from each subject support device 12 in the system 16. Depending upon the embodiment and context of use, the type of information that may be communicated between the system 16 and device 12 may include, but is not limited to, data, programs, updated software, education materials, warning messages, notifications, device settings, therapy parameters, or the like. The device communication layer 24 may include suitable routines for detecting the type of subject support device 12 in communication with the system 16 and implementing appropriate communication protocols for that type of device 12. Alternatively or in addition, the subject support device 12 may communicate information in packets or other data arrangements, where the communication includes a preamble or other portion that includes device identification information for identifying the type of the subject support device. Alternatively, or in addition, the subject support device 12 may include suitable user-operable interfaces for allowing a user to enter information, such as by selecting an optional icon or text or other device identifier, that corresponds to the type of subject support device used by that user. Such information may be communicated to the system 16, through a network connection. In yet further embodiments, the system 16 may detect the type of subject support device 12 it is communicating with in the manner described above and then may send a message requiring the user to verify that the system 16 properly detected the type of subject support device being used by the user. For systems 16 that are capable of communicating with multiple different types of subject support devices 12, the device communication layer 24 may be capable of implementing multiple different communication protocols and selects a protocol that is appropriate for the detected type of subject support device.

The data-parsing layer 26 is responsible for validating the integrity of device data received and for inputting it correctly into a database 29. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 16 may compare received identification information with pre-stored information to evaluate whether the received information is from a valid source.

The database layer 28 may include a centralized database repository that is responsible for warehousing and archiving stored data in an organized format for later access, and retrieval. The database layer 28 operates with one or more data storage device(s) 29 suitable for storing and providing access to data in the manner described herein. Such data storage device(s) 29 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. As described below, information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 16 or other entities, for analyzing group data or other forms of conglomerate data.

Embodiments of the database layer 28 and other components of the system 16 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 28 may be configured to limit access of each user to types of information pre-authorized for that user. For example, a subject may be allowed access to his or her individual medical information (with individual identifiers) stored by the database layer 28, but not allowed access to other subject's individual medical information (with individual identifiers). Similarly, a subject's authorized healthcare provider or payor entity may be provided access to some or all of the subject's individual medical information (with individual identifiers) stored by the database layer 28, but not allowed access to another individual's personal information. Also, an operator or administrator-user (on a separate computer communicating with the computing device 100) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 28 in the data storage devices 29.

In embodiments of the invention, the database layer 28 may store preference profiles. In the database layer 28, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 29 in the database layer. Illustratively, these parameters could also include analysis times for each of the meal events.

The DDMS 16 may measure, analyze, and track either blood glucose (BG) or sensor glucose (SG) readings for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 30 may include a report wizard program that pulls data from selected locations in the database 28 and generates report information from the desired parameters of interest. The reporting layer 30 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar.

In embodiments of the invention, the database layer 28 may calculate values for various medical information that is to be displayed on the reports generated by the report or reporting layer 30. For example, the database layer 28, may calculate average blood glucose or sensor glucose readings for specified timeframes. In embodiments of the invention, the reporting layer 30 may calculate values for medical or physical information that is to be displayed on the reports. For example, a user may select parameters which are then utilized by the reporting layer 30 to generate medical information values corresponding to the selected parameters. In other embodiments of the invention, the user may select a parameter profile that previously existed in the database layer 28.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs such as, but not limited to, EXCEL™ or the like. In this manner, users may import data from the system 16 into further reporting tools familiar to the user. The reporting layer 30 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 30 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 16 may allow a user generating a report to designate the report as non-printable and/or non-transferable, whereby the system 16 will provide the report in a form that inhibits printing and/or electronic transfer.

The reporting layer 30 may transfer selected reports to the graph display layer 31. The graph display layer 31 receives information regarding the selected reports and converts the data into a format that can be displayed or shown on a display 33.

In embodiments of the invention, the reporting layer 30 may store a number of the user's parameters. Illustratively, the reporting layer 30 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 32 supports interactions with the end user, for example, for user login and data access, software navigation, data input, user selection of desired report types and the display of selected information. Users may also input parameters to be utilized in the selected reports via the user interface layer 32. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 32 provides one or more websites accessible by users on the Internet. The user interface layer may include or operate with at least one (or multiple) suitable network server(s) to provide the website(s) over the Internet and to allow access, worldwide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 16, depending upon the embodiment of use.

In another example embodiment, where the DDMS 16 is located on one computing device 100, the user interface layer 32 provides a number of menus to the user to navigate through the DDMS. These menus may be created utilizing any menu format, including but not limited to HTML, XML, or Active Server pages. A user may access the DDMS 16 to perform one or more of a variety of tasks, such as accessing general information made available on a website to all subjects or groups of subjects. The user interface layer 32 of the DDMS 16 may allow a user to access specific information or to generate reports regarding that subject's medical condition or that subject's medical device(s) 12, to transfer data or other information from that subject's support device(s) 12 to the system 16, to transfer data, programs, program updates or other information from the system 16 to the subject's support device(s) 12, to manually enter information into the system 16, to engage in a remote consultation exchange with a healthcare provider, or to modify the custom settings in a subject's supported device and/or in a subject's DDMS/MDMS data file.

The system 16 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 16 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 16, based on the type of user and/or the identity of the user.

Upon entering successful verification of the user's identification information and password, the user may be provided access to secure, personalized information stored on the DDMS 16. For example, the user may be provided access to a secure, personalized location in the DDMS 16 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 12 to the system 16, manually enter additional data into the system 16, modify the subject's custom settings, and/or view and print reports. Reports may include data specific to the subject's condition, including but not limited to, data obtained from the subject's subject support device(s) 12, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 29) employed by the database layer 28.

The user may select an option to transfer (send) device data to the medical data management system 16. If the system 16 receives a user's request to transfer device data to the system, the system 16 may provide the user with step-by-step instructions on how to transfer data from the subject's supported device(s) 12. For example, the DDMS 16 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 12 used by the subject. The system 16 employs that information to select the stored instruction set(s) associated with the particular subject's support device(s) 12 for display to the user.

Other activities or resources available to the user on the system 16 may include an option for manually entering information to the DDMS/MDMS 16. For example, from the user's personalized menu or location, the user may select an option to manually enter additional information into the system 16.

Further optional activities or resources may be available to the user on the DDMS 16. For example, from the user's personalized menu, the user may select an option to receive data, software, software updates, treatment recommendations or other information from the system 16 on the subject's support device(s) 12. If the system 16 receives a request from a user to receive data, software, software updates, treatment recommendations or other information, the system 16 may provide the user with a list or other arrangement of multiple selectable icons or other indicia representing available data, software, software updates or other information available to the user.

Yet further optional activities or resources may be available to the user on the medical data management system 16 including, for example, an option for the user to customize or otherwise further personalize the user's personalized location or menu. In particular, from the user's personalized location, the user may select an option to customize parameters for the user. In addition, the user may create profiles of customizable parameters. When the system 16 receives such a request from a user, the system 16 may provide the user with a list or other arrangement of multiple selectable icons or other indicia representing parameters that may be modified to accommodate the user's preferences. When a user selects one or more of the icons or other indicia, the system 16 may receive the user's request and makes the requested modification.

Further descriptions of the DDMS/MDMS may be found in U.S. Pat. App. Pub. No. 2007/0033074, published Feb. 8, 2007, to Nitzan et al. and is entitled, "Therapy Management System", which is herein incorporated by reference in its entirety.

Figure 2A:
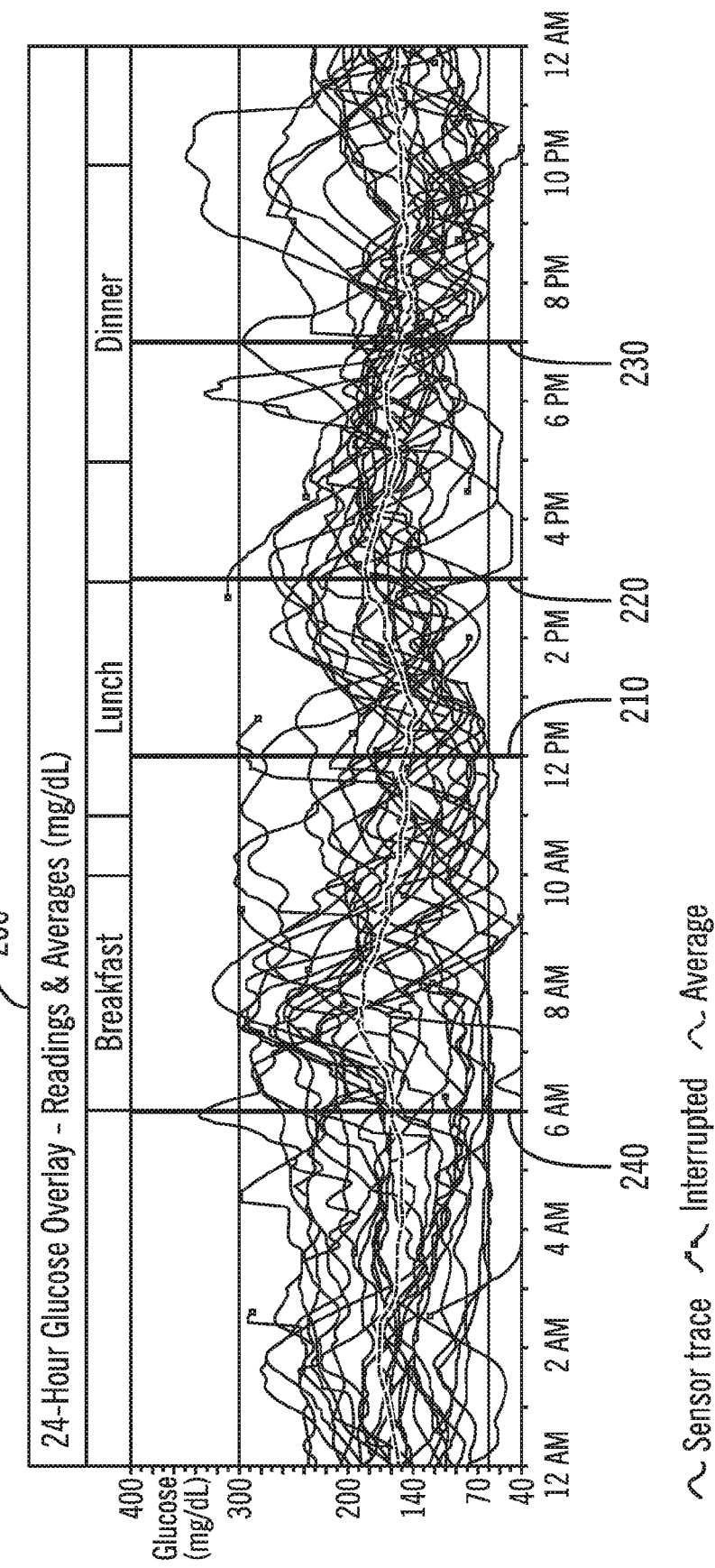
FIG. 2A illustrates a sample report displaying sensor readings according to embodiments of the present invention

FIG. 2A illustrates a report displaying sensor readings according to embodiments of the present invention. The report illustrated in FIG. 2A is a 24-Hour Glucose Overlay report 200, which may be generated by, for example, the DDMS/MDMS 16 of FIG. 1, or any other suitable system. One particular example of a suitable system is a computer executing Medtronic MiniMed's CARELINK Therapy Management Software. The sample overlay report 200 illustrates the overlaying of readings and averages of glucose values from a user for a 28-day period. In alternative embodiments, longer or shorter periods may be used, such as, but not limited to three days, one week, two weeks, three weeks, one month, two months, one quarter, six months, one year, or the life of a patient, with the choice being made to select a data set that provides a useful period of interest. The report 200 may also show the readings and averages for less than 24-hours at a time, too.

Because many people have regular schedules where event occurrences such as breakfast, lunch, dinner, afternoon naps, tea times, coffee breaks, watching the morning or evening TV news, going to bed for the night (bedtime), etc., occur each day and generally occur around the same time of day (or each day during the work week, work days only, weekends only, Sundays only, workout days only, etc.), patterns may develop based on this regular schedule. Additionally, patterns also may be analyzed based on only periodic events/conditions such as but not limited to, menstruation, non-work/school days, when administering periodic therapy, exercise, and the like; and transient events/conditions such as but not limited to, a temporary illness, having a cold, being on a particular medication, stress and anxiety, physical exertion, vacation days, holidays, etc.

By analyzing the average glucose level patterns, trends may be spotted that occur for a user relative to specific events in that user's life (e.g., breakfast, lunch, dinner, watching the evening news, etc.). For example, referring to the report 200 of FIG. 2A, we note that for this representative 28-day period, when the user has lunch at Noon shown at line 210, this user tends to experience on average a rise in glucose levels peaking around 3 PM shown at line 220, three hours after the start of lunch. Although average glucose level values are used in connection with FIG. 2A, according to embodiments of the present invention, other calculations and data sets such as standard deviations, high values, low values, etc. for a period (days, weeks, months, quarters, years, etc.), or periodic blocks of time (e.g., every fourth week, four weeks of work days, five weekends, non-working days, etc.) may be utilized as well. It is noted that glucose patterns often change during menstruation, and patterns for work days tend to be different from patterns on non-working days.

Based on this average pattern and trend, this information may be passed along to a doctor or a user, and/or to a DDMS/MDMS, an infusion pump, a controller/programmer, or any other suitable device, for example, which may take proactive measures in recommending and/or automatically delivering a bolus of insulin in advance of this predicted rise and peak shown at line 220 (e.g., a notification event that the user should be made aware of, and/or to take appropriate action) if a rise in glucose levels begins to occur, e.g., an hour after lunch. If the user normally takes lunch at Noon but one day is caught in a meeting that runs longer, and the user takes lunch at 1 PM instead, the infusion pump (or any other suitable device), for example, may make a prediction as to the upcoming rise and peak shown at line 220 based on the average glucose level pattern derived from the report 200 of FIG. 2A and time-shift the pattern one-hour later, such that it will predict a rise and peak at 4 PM instead of 3 PM, and take proactive measures in recommending and/or delivering a bolus in advance of this predicted rise and peak if it starts to notice a rise in glucose levels an hour after taking lunch at 1 PM. Alternatively, the basal rate of insulin delivery may be temporarily increased to match this rise and peak following lunch taken at 1 PM, an hour later than usual (e.g., a "lunch time" basal rate pattern, a "dinner time" basal rate pattern, etc.). Further description of an insulin infusion device having the capability to deliver time-shifted basal insulin may be found in U.S. Pat. App. Pub. No. 2007/0112298, published May 17, 2007, to Mueller et al. and entitled "External Infusion Device with Programmable Capabilities to Time-Shift Basal Insulin and Method of Using the Same", which is herein incorporated by reference in its entirety.

By predicting the occurrence of a notification event (e.g., a rise and/or peak), more accurate treatment and delivery of insulin may be accomplished to better keep a user within a preferred glucose level range, but additionally, occurrences of severe adverse events (SAEs) may be minimized. Typically, a particular pattern occurs just before an SAE occurs, and if the DDMS/MDMS, infusion pump, or other suitable device, recognizes the pre-SAE pattern developing, the user may be alerted of a potential SAE occurring and preventive measures may be taken to minimize or eliminate the occurrence of the SAE, even automatically without user input, if necessary according to embodiments of the present invention.

Although an average glucose level pattern for a 24-hour period may be used, the 24-hour pattern may be partitioned into multiple patterns anchored around triggering events (event occurrences) as reference points, e.g., a pattern for breakfast to lunch (morning pattern), a pattern from lunch to dinner (afternoon pattern), and a pattern from dinner to breakfast (evening pattern), for time shifting. Meal times and meal boluses (including correction boluses) serve as good triggering events, but any other suitable event occurrence (especially those events that occur regularly in a user's life around the same time each day) may be utilized as well for the purposes of establishing common points of reference for the time-shifting of a pattern. Alarms, for example, are often followed by a bolus event, and high glucose level alarms may serve as a triggering event occurrence, too. According to embodiments of the present invention, the patterns also may be sorted by weekdays only, weekends only, a particular day only (e.g., Wednesdays only), sick days only, exercise/workout days only, etc.

Accordingly to embodiments of the present invention, the user may inform the DDMS/MDMS, infusion pump, controller/programmer, or any other suitable device, that he/she is about to have lunch, and the infusion pump, for example, may acknowledge and record the occurrence of this triggering event to perform any time-shifting of a pattern as necessary. Alternatively, the DDMS/MDMS, infusion pump, controller/programmer, or any other suitable device may deduce when a meal is about to be taken based on a user initiated bolus delivery and the time it occurred (e.g., around 7 AM for breakfast, or around Noon for lunch, etc.). Knowing how much insulin was delivered for a meal may be as relevant as knowing the type of meal, for example, breakfast, lunch, or dinner, consumed. Moreover, the type of bolus selected and administered by the user (e.g., a normal, square wave, dual wave, a correction bolus, etc.) along with the type of food ingested at that time may also permit the DDMS/MDMS, infusion pump, controller/programmer, or any other suitable device to deduce that the user may have certain issues with particular foods (e.g., fatty foods).

By identifying and performing time-shifting of patterns, we may make better predictions as to the glucose levels of a diabetic and allow a doctor to take proactive measures to provide more accurate treatment to keep more stable glucose levels within the desired range. Severe adverse events (SAEs) may be minimized or eliminated by recognizing the pre-SAE pattern leading up to SAEs in the past. The use of A1c testing may further assist in determining whether glucose levels have been within desirable ranges for a longer period of time (e.g., about three months). According to embodiments of the present invention, alarms may be set up on an infusion pump to match a typical user SAE pattern, and the alarm may sound when such a SAE pattern is observed.

To make a pattern more accurate, anomalous data may be removed or filtered from the data points making up the pattern ("clipping"), as the anomalous data may not be representative of a person's typical day. For example, referring to the report 200 of FIG. 2A, if the user had a few days where his/her schedule was completely atypical of a regular work day (perhaps flying cross-country on a business trip), we may exclude the glucose level readings for these non-routine days as they are not typical of a "regular" work day (it is likely that the user had a meal or two during the business trip, but, these meals may not have occurred at the same usual times the user typically has these meals, and/or the meals may be of different types, portions, etc. that the user typically has). That is, rare events and anomalous data generally should not dictate the direction of therapy based on patterns. According to embodiments of the present invention, the data also may be filtered by a particular day of the week (e.g., remove all Wednesday data), a day each month (e.g., remove all data on the 15$^{th}$), a type of day (e.g., remove all data on exercise/workout days), by particular time of day (e.g., remove all data from 12 AM to 3 AM), by a particular week, month, etc., or any combination thereof.

Conversely, there are situations where investigating outlying/anomalous events may assist in determining behavioral issues that may have an impact on the course of therapy, and determining causes of an outlying event may be helpful in reducing these anomalous occurrences that may be detrimental to therapy. According to embodiments of the present invention, the data set may also be filtered such that all glucose level readings falling into one or more patterns is removed, leaving only the anomalous data for analysis.

The reports/charts illustrated in FIGS. 2B-2K may be representative of snapshot screens displayed on a DDMS/MDMS executing, for example, Medtronic MiniMed's CARELINK™ Therapy Management Software, or any other suitable software, as described in connection with FIG. 1 above, to assist a doctor in planning a course of treatment (and in some instances, accessible to a user, too). Although the charts illustrated in FIGS. 2B-2I and 2K show the glucose readings from 11 AM to 9 PM, longer or shorter periods may be displayed according to embodiments of the present invention. The charts in FIGS. 2B-2I and 2K, as illustrated, may be portions of the 24-hour report illustrated in FIG. 2A. For instance, in other embodiments, a 1-hour, 2-hour, 3-hour, 4-hour, 5-hour, 6-hour, 7-hour, 8-hour, 9-hour, 10-hour, 11-hour, or 12-hour portions of a 24-hour day report may be used, and 2 days, 3 days, 4 days, 5 days, 6 days, a week, 2 weeks, 3 weeks, 4 weeks, a month, a quarter, or the like reports may be used as well.

Although only four representative glucose reading lines are illustrated in each of FIGS. 2B-2J, an actual chart viewed by a doctor often displays many more lines (20 to 30, or more), and while only four lines are represented in FIGS. 2B-2J to simplify and make the charts easier to read for illustrative purposes, according to embodiments of the present invention, any number of lines may be overlaid on the charts. Lines 252, 254, 256, and 258 in FIG. 2B (and similarly for the corresponding lines in FIGS. 2C-2J) may each represent raw glucose level readings for a day, filtered, smoothed, etc. readings for a day, several days, weeks, months, etc., or any combination thereof. A chart including the average value of the raw glucose level readings, standard deviation (once the average has been determined), high-low lines, etc., for example, as illustrated in FIG. 2K and discussed in further detail below, also may be generated.

According to embodiments of the present invention, additional data may be further shown in the charts of FIGS. 2B-2K as well, for example, a basal insulin profile and a bolus delivery graph. Moreover, a doctor or user may select any one of the readings (e.g., lines 252, 254, 256, 258 in FIG. 2B) displayed on the charts by the DDMS/MDMS to obtain further data associated with the selected reading (e.g., high/low values, averages, standard deviation, number of meter reads, total insulin, number of boluses, prime volume, time in temporary basal, time in suspension, etc.), which may be displayed on a separate screen. Further description of data that may be displayed on a screen by the DDMS/MDMS may be found in U.S. Pat. App. Pub. No. 2002/0193679, published Dec. 19, 2002, to Malave et al. and entitled "Communication Station and Software for Interfacing with an Infusion Pump, Analyte Monitor, Analyte Meter, or the Like", which is herein incorporated by reference in its entirety.

Generally speaking, the more data that is available to a doctor, the more accurate and better the treatment may be planned for a user. However, the more data that is displayed on a screen at once (e.g., daily 24-hour glucose sensor readings for a three-month period will have over 90 lines moving up and down the chart), the more difficult it is for a doctor or other viewer to read and comprehend, especially if the data does not readily appear to convey any trends or patterns on which a doctor may base a course of treatment. Having more data available also increases the chances that more "noise" data will be introduced into the overall data set. In particular, a doctor using a DDMS/MDMS displaying a glucose readings overlay report (e.g., as in FIG. 2A) may have data spanning a period of days, weeks, months, and/or years for a single patient. This amount of data displayed on a screen all at once is overwhelming, confusing, and difficult to read and understand without some filtering and organization. This raw data becomes not particularly useful on its face without further analysis. No meaningful treatment plan may be formulated based on a chart of numerous glucose readings, such as shown in FIG. 2A, that seemingly has no relation to each other. If the numerous glucose level readings displayed may be sorted, for example, by similar like patterns, and/or around particular event occurrences (e.g., breakfast, lunch, or dinner), the doctor will have a more meaningful chart where certain glucose level patterns may be perceived on which he/she may develop a course of treatment.

As discussed above, many people have regular schedules where event occurrences such as breakfast, lunch, dinner, afternoon naps, tea times, coffee breaks, watching the morning or evening TV news, going to sleeping/bedtime, waking up, etc., that tend to occur each day and generally around the same time of day (or each day during the work week, work days only, weekends only, Sundays only, workout days only, etc.). Knowing when these events occur is particularly helpful in analyzing the raw data. Using these events (e.g., breakfast, lunch, dinner, watching the evening news, etc.) as markers and reference/anchoring points in time (e.g., starting points, mid-points, end points) to adjust or filter the glucose level readings amongst all of the readings relative to each common event occurrence will allow an analysis where trends and patterns may be perceived. In one representative example according to embodiments of the present invention, the glucose level readings may be lined up starting from when the user initiates a lunch time meal bolus, a correction bolus, a particular bolus type (e.g., normal, square wave, dual wave), etc., and the DDMS/MDMS may analyze the glucose level readings from the start of the meal bolus (e.g., up to the start of the next common event occurrence of, e.g., a dinner time meal bolus) to determine whether patterns exist, take an average reading, etc. The glucose level readings also may be lined up based on any suitable event occurrence, including but not limited to meal boluses, correction boluses, meal times, bedtimes, exercise, intake of medications, etc. The readings may be shifted and lined up on an existing time scale, for example, as illustrated in FIG. 2C, or according to embodiments of the present invention, using a relative time scale zeroed to the start of a particular event occurrence, for example, as illustrated in FIG. 2J and discussed in further detail below.

The DDMS/MDMS may generate a variety of patterns from the glucose level readings anchored around particular event occurrence(s). Glucose level readings that seem to fall outside of any particular pattern (e.g., anomalous readings) may be further analyzed, or filtered out and discarded. Alternatively, only the anomalous readings may be shown. Suitable pattern recognition algorithms (e.g., utilized in defense/weapon systems, astronomy, computer science, etc.) may be modified to be used to analyze the plurality of glucose level readings for a user, and according to embodiments of the present invention, to analyze the readings after each common event occurrence amongst all or most of the readings to determine whether any patterns or trends exist.

The pattern recognition algorithm may recognize a seemingly "anomalous" glucose level reading that fits a particular pattern or shape formed by a plurality of other glucose level readings around a particular event occurrence (e.g., a pattern formed by the readings starting when the user takes lunch each day). This anomalous reading may appear to be, for example: (1) skewed a couple hours ahead of or behind the particular pattern, (2) having a greater positive and/or negative magnitude than the particular pattern, (3) compressed or stretched in time than the particular pattern, (4) skewed upwards or downwards from the basal glucose level of the particular pattern, or any combination thereof. By recognizing a potential glucose level reading falling "out-of-pattern" from a particular pattern formed by the other glucose level readings, this out-of-pattern reading may be adapted to fit with the rest of the glucose level readings forming the pattern by making adjustments to the out-of-pattern glucose level reading, thus preserving that glucose level reading for analysis.

Alternatively, the out-of-pattern glucose level reading may be analyzed on its own merits to determine potential causes of such an out-of-pattern reading and any other potential issues associated therewith, which may be helpful in learning the behavior of a user and in making any adjustments to his/her therapy as necessary to minimize further out-of-pattern readings. Moreover, the patterns may be in themselves further sorted and filtered by the types of readings forming the patterns, for example, a "weekday only" pattern (formed from weekday only readings), a "weekend only" pattern (formed from weekend only readings), "Wednesdays" pattern (formed from Wednesdays only readings), etc.

Although the existence of an event occurrence as a marker for a glucose level reading is helpful in establishing a reference point for the pattern recognition software to analyze for patterns, an event occurrence is not always necessary for the pattern recognition software and may not always be available for each glucose level reading. It is possible that a meal/correction bolus event occurrence was not recorded by, for example, the infusion device or controller/programmer, because the user self-administered a bolus with a manual shot via a needle and syringe. Secondly, the user may have forgotten to enter an exercise event occurrence marker when the user exercised. Thirdly, the user may have just missed administering a bolus, leaving no event occurrence marker of one, or the bolus may have been administered but was not recorded. The administered bolus may have been the wrong type, too much, too little, etc., such that it makes the event occurrence marker corresponding to that administered bolus unhelpful for purposes of analysis.

Even absent an event occurrence marker in the glucose level readings, the pattern recognition software may still analyze a glucose level reading, for example, by determining whether there is a match in the rising/falling slope of the reading, in the overall shape of the reading, the overall size/magnitude of the reading, etc., with other glucose level readings, with or without event occurrence markers, forming a particular pattern.

Figure 2B:
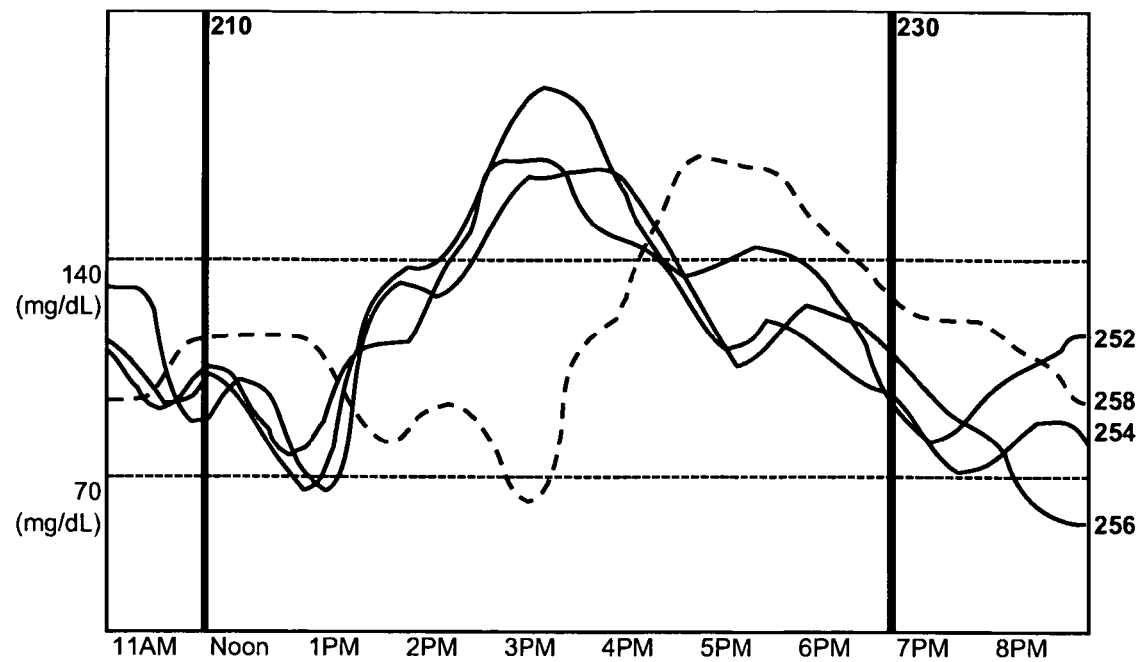
FIG. 2B illustrates a sample report displaying sensor readings according to embodiments of the present invention.
Figure 2C:
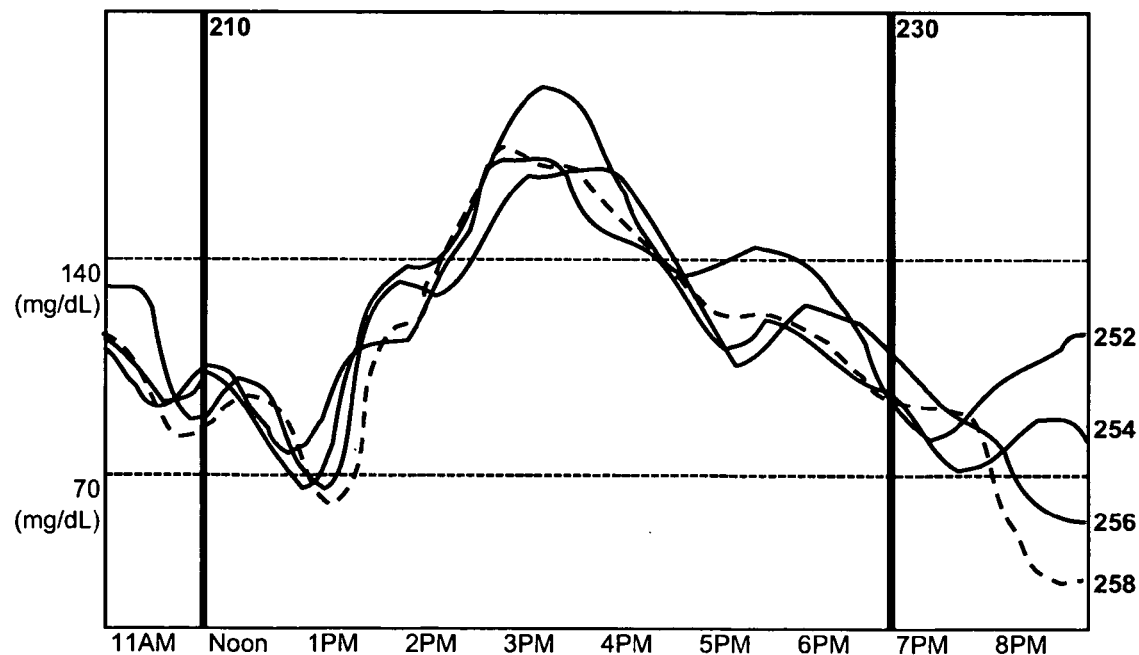
FIG. 2C illustrates an adapted time-shifted sample report displaying sensor readings from FIG. 2B according to embodiments of the present invention.

As illustrated in the simplified representative glucose overlay chart of FIG. 2B, four representative glucose level reading lines 252, 254, 256, 258 are shown. By analyzing the data in the chart of FIG. 2B, the DDMS/MDMS may determine that a pattern of two small successive dips followed by a large rise in glucose levels exist for lines 252, 254, 256, and 258. This particular pattern of dips and rises is merely an illustrative example, and according to embodiments of the present invention, any other patterns and types of patterns may be analyzed. Line 258 appears to be an anomaly such that its two small successive dips followed by a rise occur a couple hours later than at lines 252, 254, 256, but otherwise follows a similar shape as the pattern formed by lines 252, 254, 256.

To use as much of the available data as possible, the DDMS/MDMS may try to adapt or "fit" the anomalous data to an existing pattern(s). By recognizing the general pattern formed by lines 252, 254, 256 and that of anomalous line 258, the DDMS/MDMS may determine that by shifting the anomalous line 258 back two hours in time (to match the data obtained when the user typically takes lunch), as illustrated in FIG. 2C, the reading of line 258 generally conforms with the pattern established by lines 252, 254, 256, especially from the period of Noon to 7 PM. The time-shifting may be performed, for example, if we knew that the user took lunch two hours later at 2 PM than his/her usual time at Noon when the reading for line 258 was taken (discussed in further detail below). By time-shifting line 258, an additional set of data may be utilized for analysis. The doctor may see that the user tends to rise and peak around 3 PM, and a course of treatment may be tailored towards this trend and attempt to reduce this spike and keep the glucose levels more stable and within the desired range.

The DDMS/MDMS may automatically attempt to conform data sets (e.g., each glucose level reading) to an entire 24-hour period, or any portion thereof, e.g., to generate a "morning" pattern, "afternoon" pattern, "evening" pattern, or the like. The patterns are more robust if more data is available, and by conforming anomalous data to existing data sets for a pattern, the therapy may be more accurate. In a perfect situation (but not likely), every glucose level reading falls into at least one pattern, with or without adjustment of the glucose level readings by the DDMS/MDMS. Having a chart of organized patterns for all or most of the data greatly assists the doctor in observing trends and preparing the best course of treatment for the user. However, if anomalous data cannot be properly conformed, that is, it does not appear to fit any of the patterns, the anomalous data may be filtered out and not utilized in the analysis. For example, the adapted time-shifted pattern in the chart of FIG. 2C may be utilized to generate an average "afternoon" pattern for analysis by a doctor to help the user in keeping stable glucose levels and within the desired range. Additionally, general trends or ideal patterns may be overlaid onto an existing report to show how close the user is to such ideal or population average levels, and to highlight areas where the user may want to make changes affecting his/her glucose levels.

Moreover, according to embodiments of the present invention, a doctor or user may select the criteria and parameters to filter and analyze the glucose level readings. A doctor or user may also select whether a particular pattern should be included or excluded from analysis. According to embodiments of the present invention and as discussed above, a doctor or user may click on any one of the glucose level readings (e.g., lines 252, 254, 256, 258 in FIG. 2B) and obtain further data relating to this selected reading, and enter notes or comments regarding this selected reading that may be stored by the DDMS/MDMS (e.g., indicating an unmarked event, explanation of a particular behavior, etc.). Alternatively, a doctor or user may select/click one or more of the displayed lines and delete them for the purposes of not including the selected lines in the analysis (e.g., to generate the average, standard deviations, etc.). For example, the clinician may realize that some days have very unusual data due to unusual circumstances in the patient's life, such as, e.g., stress due to a car accident, an emotional event, unusual physical exertion, unusual meals due to a celebration or travel, and the like. By eliminating these unusual data sets, the usual data sets remain, which the clinician may use to analyze and plan a course of therapy.

The glucose level analysis may be further enhanced if we know, by direct user input (e.g., setting a "lunch" event occurrence marker) or inferred from a user action (e.g., administering a meal bolus in the afternoon to have lunch), that the user took lunch at Noon on the days (weeks, months, etc.) that lines 252, 254, 256 were read; and that for line 258, the user took lunch a couple hours later around 2 PM versus at Noon. Additionally, the DDMS/MDMS may recognize that line 258 follows a particular pattern and/or shape that falls within a "lunch time" pattern, and a start time of when the user took lunch for that particular line 258 may also be inferred and calculated based on pattern recognition algorithms according to embodiments of the present invention. This type of information would further strengthen the pattern recognition and filtering scheme performed by the DDMS/MDMS in generating an "afternoon" pattern anchored around when the user takes lunch. For example, an understanding or analysis may be developed to reduce the rise and peak that occurs about two hours after the user eats in the afternoon, whether it is always at Noon, or at another time, for example, by setting a temporary basal rate to be utilized when taking lunch to reduce the observed rise and peak.

FIG. 2J illustrates an adapted time-shifted sample report displaying sensor readings from FIG. 2C utilizing a relative time line according to embodiments of the present invention. A relative time line chart, fixed at, for example, an event occurrence such as a meal bolus, start of lunch (line 210), etc., may be generated by the DDMS/MDMS for analysis by a doctor. A notification event occurring after a time span from an event occurrence, and anomalies, are more readily discernible using a relative time line chart as in FIG. 2J. Any time increments other than one hour (e.g., 2-hours, minute(s), day(s), week(s), month(s), quarter(s), year(s), etc.) and for any period in time may be utilized, too. According to embodiments of the present invention, the relative time line chart of FIG. 2J may be equally applicable to any of the charts illustrated in FIGS. 2A-2I and 2K.

FIG. 2K illustrates a report showing an average glucose level reading, standard deviation, and high-low lines for the adapted time-shifted report of FIG. 2C according to embodiments of the present invention. The DDMS/MDMS may generate a chart displaying an average glucose reading 292 based on the adapted glucose level readings 252, 254, 256, 258 of FIG. 2C. Once an average is determined, the DDMS/MDMS may also present the standard deviation lines 294, 296 as illustrated in FIG. 2K according to embodiments of the present invention. Furthermore, high-low lines 298 of the adapted glucose level readings of lines 252, 254, 256, 258 of FIG. 2C also may be generated. Any other types of data calculations other than those discussed above also may be performed by the DDMS/MDMS and displayed for review by a doctor or user. According to embodiments of the present invention, the display of average glucose level readings, standard deviation, and high-low lines, as in the chart of FIG. 2K, independently, combined, or with other data calculations may be equally applicable to any of the charts illustrated in FIGS. 2A-2J. For example, an average of a group of lines may be calculated, and then the error for each line compared to the average may be calculated. One method of calculation involves calculating the average line using all but one of the lines, and then calculate the error between the average and the line that was ignored; this process is repeated for all the groups of lines, and then the lines with the greatest errors may be determined. If a particular line or group of lines have significantly greater errors compared to the average, then the average may be recalculated by omitting these lines that have greater errors compared to the average. These lines having greater errors may be automatically removed from analysis, or they may be highlighted such that a clinician may elect to keep or remove them from analysis. Analysis on only the lines having greater errors may be also performed, too.

Figure 2D:
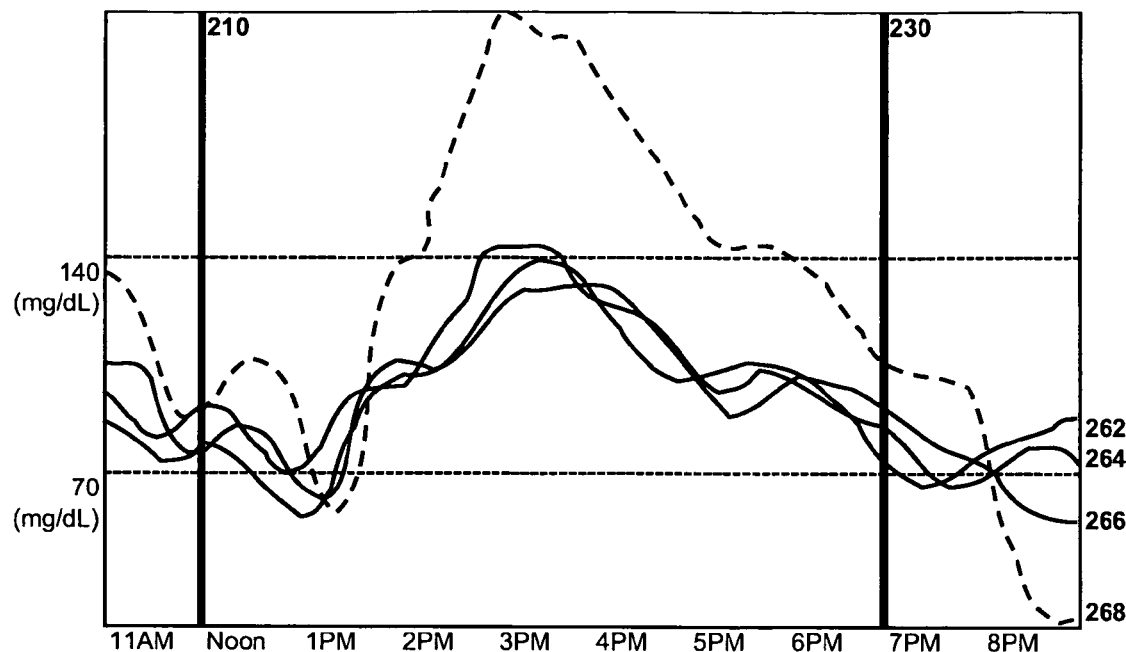
FIG. 2D illustrates a sample report displaying sensor readings according to embodiments of the present invention.

FIG. 2D illustrates a sample report displaying sensor readings according to embodiments of the present invention. Similar to the chart of FIG. 2B above, the chart of FIG. 2D shows three representative lines 262, 264, 266 forming a general pattern, with anomalous line 268 showing an extremely high rise and peak at around 3 PM and a long downward crash towards 8 PM. By analyzing the data in the chart of FIG. 2D, the DDMS/MDMS may determine that anomalous line 268 exhibits a similar pattern as formed by lines 262, 264, 266, except that the glucose level readings of line 268 are more acute and severe in the magnitude of the rise and fall of the glucose levels. Due to any set of events for the particular day (week, month, etc.) that the reading for line 268 was taken, the user may have been particularly sensitive to foods ingested, the user administered a different meal bolus dosage, etc., and caused the anomalous reading of line 268. Alternatively, the anomalous reading of line 268 may have been caused by a hardware issue, for example, by a bias or an overly-sensitive sensor, or by improper operation by the user that exaggerated the readings, or the sensor was mis-calibrated by the user. A hardware issue may be identified, for example, if a set of readings obtained from when the sensor was placed on the user all exhibited similar increased magnitudes, or if there is a known sensitivity with a particular sensor lot number.

One way of determining whether a sensor may be overly sensitive or whether there might have been a calibration issue is to analyze the raw electrical current signal values ($I_{sig}$) received from the sensor (typically, the higher the $I_{sig}$ value, the higher levels of glucose detected). These values may be stored by, for example, the DDMS/MDMS or any other suitable system. For example, if the $I_{sig}$ values from which the anomalous reading of line 268 was derived was consistent with and matches the range of the $I_{sig}$ values for lines 262, 264, 266, a mis-calibrated sensor may be at issue. But if the $I_{sig}$ values for anomalous line 268 are not consistent with the $I_{sig}$ values for lines 262, 264, 266, for example, if the $I_{sig}$ values for line 268 also share the increased magnitudes like line 268 relative to the $I_{sig}$ values for lines 262, 264, 266, then it is possible that the sensor hardware has a bias or is overly sensitive.

Figure 2E:
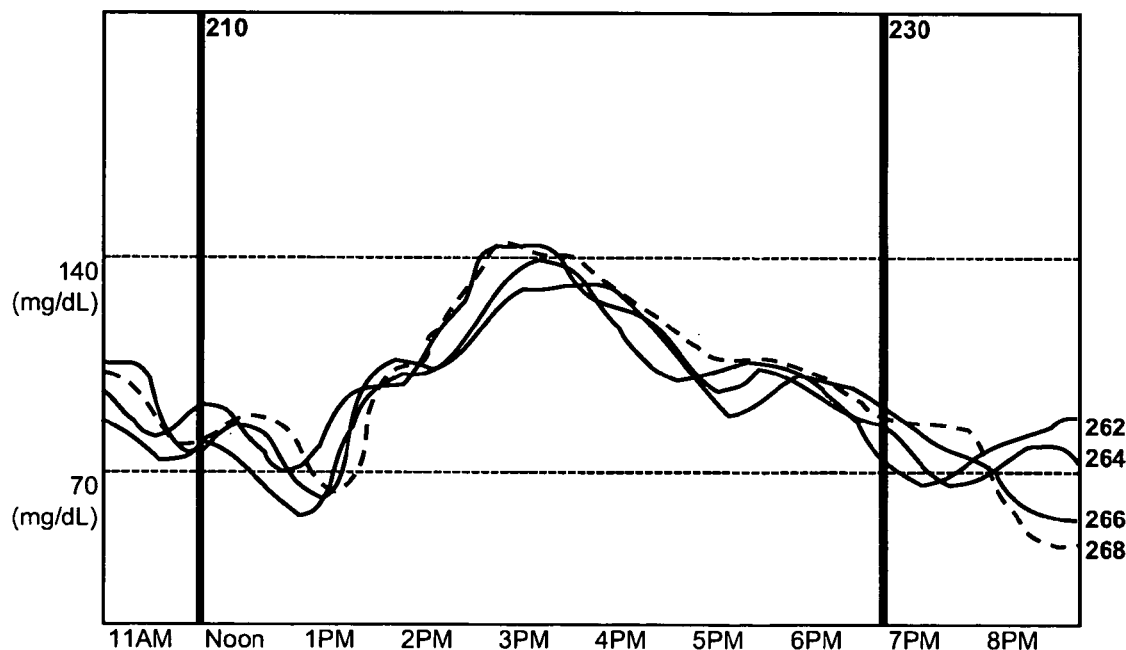
FIG. 2E illustrates an adapted glucose-level-compressed sample report displaying sensor readings from FIG. 2D according to embodiments of the present invention.

By recognizing the general pattern formed by lines 262, 264, 266 and that of anomalous line 268, the DDMS/MDMS may determine that by compressing the anomalous line 268 towards the center target range of desired glucose levels (70 mg/dL to 140 mg/dL), as illustrated in FIG. 2E, the reading of line 268 generally conforms to the pattern formed by lines 262, 264, 266, especially from the period of Noon to 7 PM. For example, if it is determined that the sensor used to obtain the anomalous reading of line 268 was overly sensitive and was providing exaggerated readings in magnitude, compressing anomalous line 268 would normalize this reading to one that would have been obtained had a normally sensitive sensor been used. By compressing line 268 in both directions inwards towards the desired glucose level range, an additional set of data, which was previously considered anomalous and potentially filtered out and excluded, may be included for analysis.

As discussed above with respect to FIGS. 2B and 2C, the analysis may be further enhanced if we know, by direct user input (e.g., setting a "lunch" event occurrence marker) or inferred from a user action (e.g., administering a meal bolus in the afternoon to have lunch), that the user took lunch at Noon on the days (weeks, months, etc.) that lines 262, 264, 266, 268 were read. This type of information would further strengthen the pattern recognition and filtering scheme performed by the DDMS/MDMS in knowing that the reading of line 268 was consistent in time with when the user typically took lunch and that time-shifting in this instance may be unnecessary in the present example (see, e.g., FIG. 2D, that the user may have been just particularly sensitive to foods ingested when the reading of line 268 was taken, underestimated the insulin bolus required for a meal, delayed a bolus of insulin until the glucose level was already increasing, or that an overly sensitive, improperly operated, or mis-calibrated sensor was used), in generating the adapted glucose-level-compressed chart of FIG. 2D.

Figure 2F:
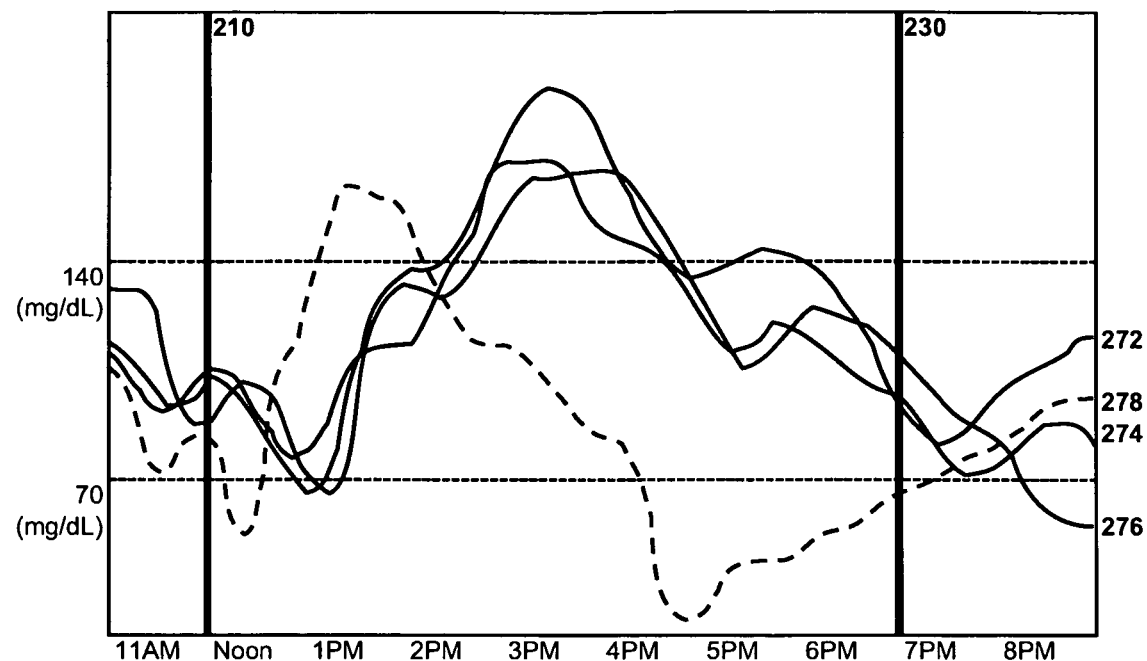
FIG. 2F illustrates a sample report displaying sensor readings according to embodiments of the present invention.

FIG. 2F illustrates a sample report displaying sensor readings according to embodiments of the present invention. Similar to the charts of FIGS. 2B and 2D above, the chart of FIG. 2F shows three representative lines 272, 274, 276 forming a general pattern, with anomalous line 278 showing a rise and peak within about an hour's time, as opposed to about two hours for lines 272, 274, 276. By analyzing the data in the chart of FIG. 2F, the DDMS/MDMS may determine that anomalous line 278 exhibits a similar pattern as formed by lines 272, 274, 276, except that the readings of line 278 appear to have the glucose levels rise and fall at a more rapid rate. Due to any set of events for the particular day (week, month, etc.) that the reading for line 278 was taken, the user experienced a more rapid rise and fall of glucose levels (e.g., eaten lunch in a quarter of the time as usual, ate a different portion and/or type of food, etc.) in the afternoon that caused the anomalous reading of line 278.

Figure 2G:
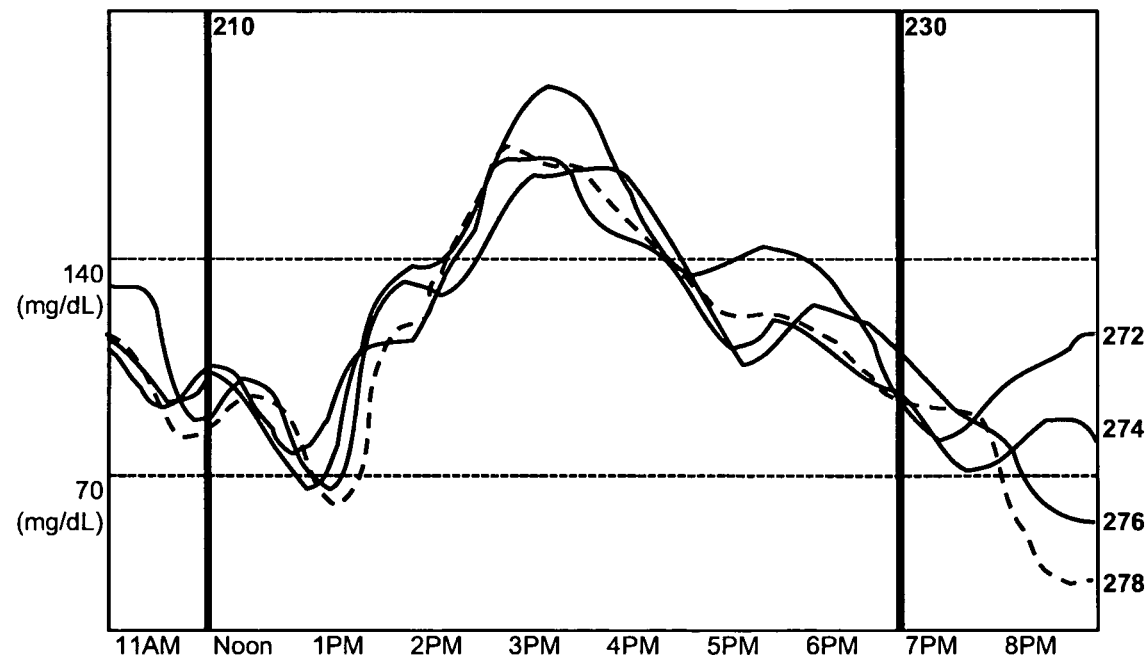
FIG. 2G illustrates an adapted time-stretched sample report displaying sensor readings from FIG. 2F according to embodiments of the present invention.

By recognizing the general pattern formed by lines 272, 274, 276 and that of anomalous line 278, the DDMS/MDMS may determine that by stretching the anomalous line 278 in time, as illustrated in FIG. 2G, the reading of line 278 generally conforms to the pattern formed by lines 272, 274, 276, especially from the period of Noon to 7 PM. According to embodiments of the present invention, we are interested analyzing a "typical" lunch pattern in the present example, and the time-stretching of line 278 would normalize this reading to one that would have been obtained had a typical lunch been taken. Alternatively, a separate analysis may be performed on the anomalous line 278 itself, or in combination with other readings. By time-stretching line 278, an additional data set, which was previously considered anomalous and potentially filtered out and excluded, may be included for analysis.

Figure 2H:
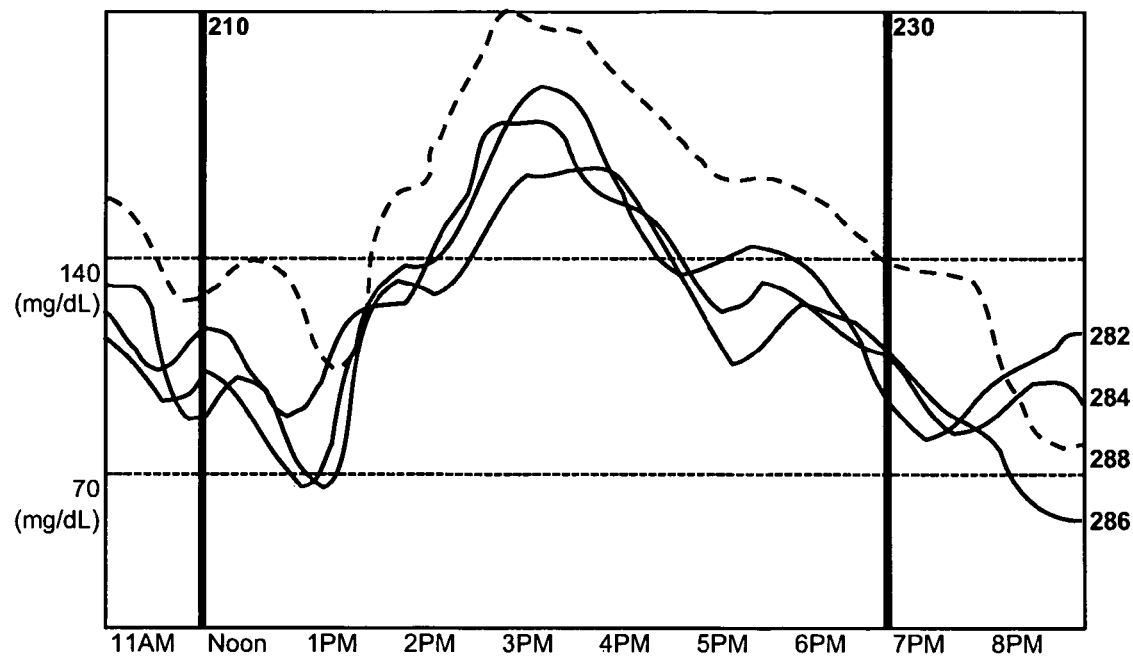
FIG. 2H illustrates a sample report displaying sensor readings according to embodiments of the present invention.

FIG. 2H illustrates a sample report displaying sensor readings according to embodiments of the present invention. Similar to the charts of FIGS. 2B, 2D, and 2F, the chart of FIG. 2H shows three representative lines 282, 284, 286 forming a general pattern, with anomalous line 288 having generally skewed high glucose levels. By analyzing the data in the chart of FIG. 2H, the DDMS/MDMS may determine that anomalous line 288 exhibits a similar pattern as formed by lines 282, 284, 286, except that the readings of line 288 are mostly above the desired glucose levels for the entire period illustrated in the chart of FIG. 2H. Due to any set of events for the particular day (week, month, etc.) that the reading for line 288 was taken, the user was having high glucose baseline levels that caused the anomalous reading of line 288. For example, the user may have set a lower basal insulin rate/pattern, which caused all of the glucose level readings to skew upwards on the higher end since the user made the basal insulin rate/pattern change.

Alternatively, according to embodiments of the present invention, the DDMS/MDMS may detect that the glucose level readings for the past few days have been skewed on the high side, which may infer that there may be a problem with the sensor (e.g., the sensor may be overly sensitive, improperly operated, mis-calibrated, etc.), and the user may be alerted to check the sensor to make sure that it is functioning properly. Any suitable techniques to diagnose a potentially overly sensitive or improperly operated sensor, or identify a mis-calibration, including analyzing the $I_{sig}$ values as discussed above with respect to FIGS. 2D and 2E, may be utilized.

Figure 2I:
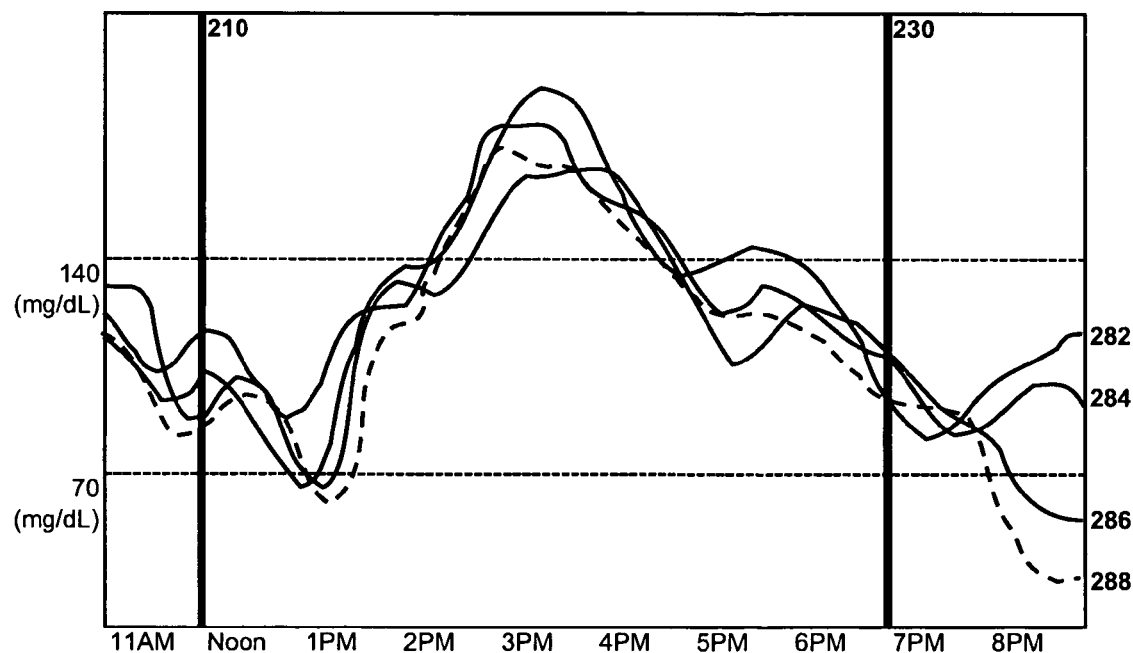
FIG. 2I illustrates an adapted glucose-level-shifted sample report displaying sensor readings from FIG. 2H according to embodiments of the present invention.
Figure 2J:
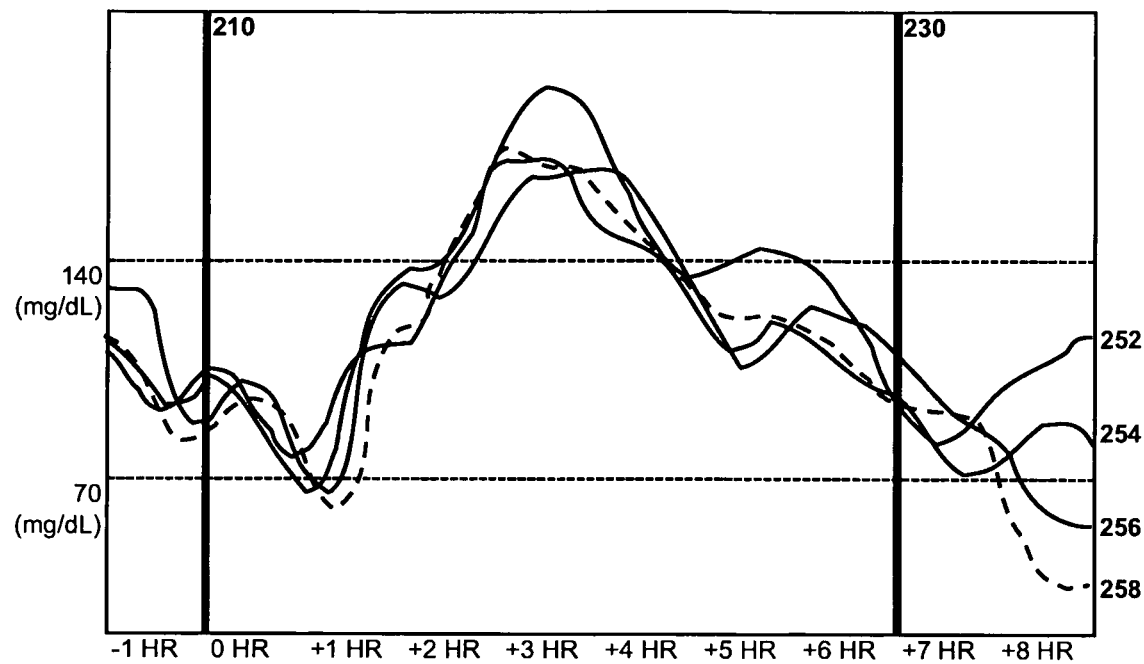
FIG. 2J illustrates an adapted time-shifted sample report displaying sensor readings from FIG. 2C utilizing a relative time line according to embodiments of the present invention.
Figure 2K:
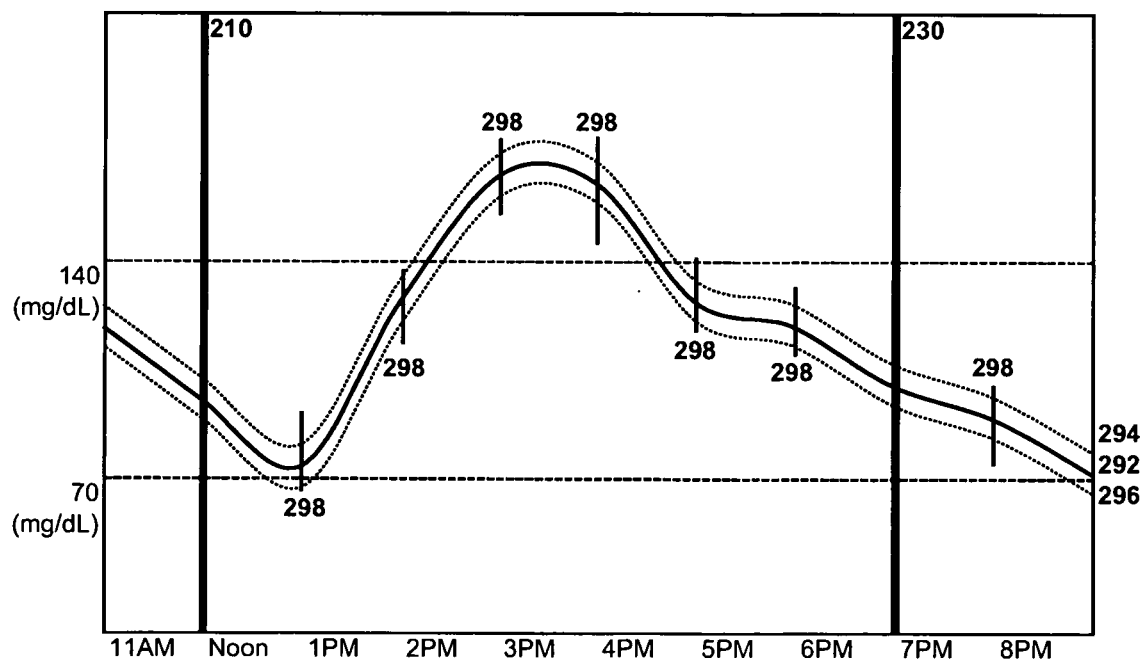
FIG. 2K illustrates a report showing an average glucose level reading, standard deviation, and high-low lines of the adapted time-shifted sample report of FIG. 2C according to embodiments of the present invention.

By utilizing pattern recognition algorithms to determine the general pattern formed by lines 282, 284, 286 and that of anomalous line 288, the DDMS/MDMS may determine that by shifting downwards the anomalous line 288 towards the center target range of desired glucose levels (as the user was "running high" due to being ill or under stress, or perhaps due to an overly sensitive, improperly operated, or mis-calibrated sensor, or a lowered basal insulin rate, etc.), as illustrated in FIG. 2I, the reading of line 288 generally conforms to the pattern formed by lines 282, 284, 286, especially from the period of Noon to 7 PM. By shifting downwards line 288, an additional data set, which was previously considered anomalous and potentially filtered out and excluded, may be included in the analysis.

Although the anomalous lines 258, 268, 278, 288 in FIGS. 2B and 2C, 2D and 2E, 2F and 2G, and 2H and 2I, respectively, were adapted by the DDMS/MDMS by making a single adjustment (i.e., time-shift, compress by glucose level, stretch by time, shift by glucose level) to the anomalous lines 258, 268, 278, 288, according to embodiments of the present invention, the DDMS/MDMS may make more than a single adjustment (e.g., time-shift and compress by glucose level, stretch by time and shift by glucose level, etc., or any combination thereof), and/or make other types of adjustments than those discussed above, to one or more of the lines as appropriate. Moreover, these adjustments may be made for glucose level readings in any other time period other than from 11 AM to 9 PM, as illustrated in FIGS. 2B-2I and 2K, too. An anomalous reading not adapted to a pattern by the DDMS/MDMS may be filtered out and excluded from analysis, or analyzed separately, independently or with other readings.

Figure 3:
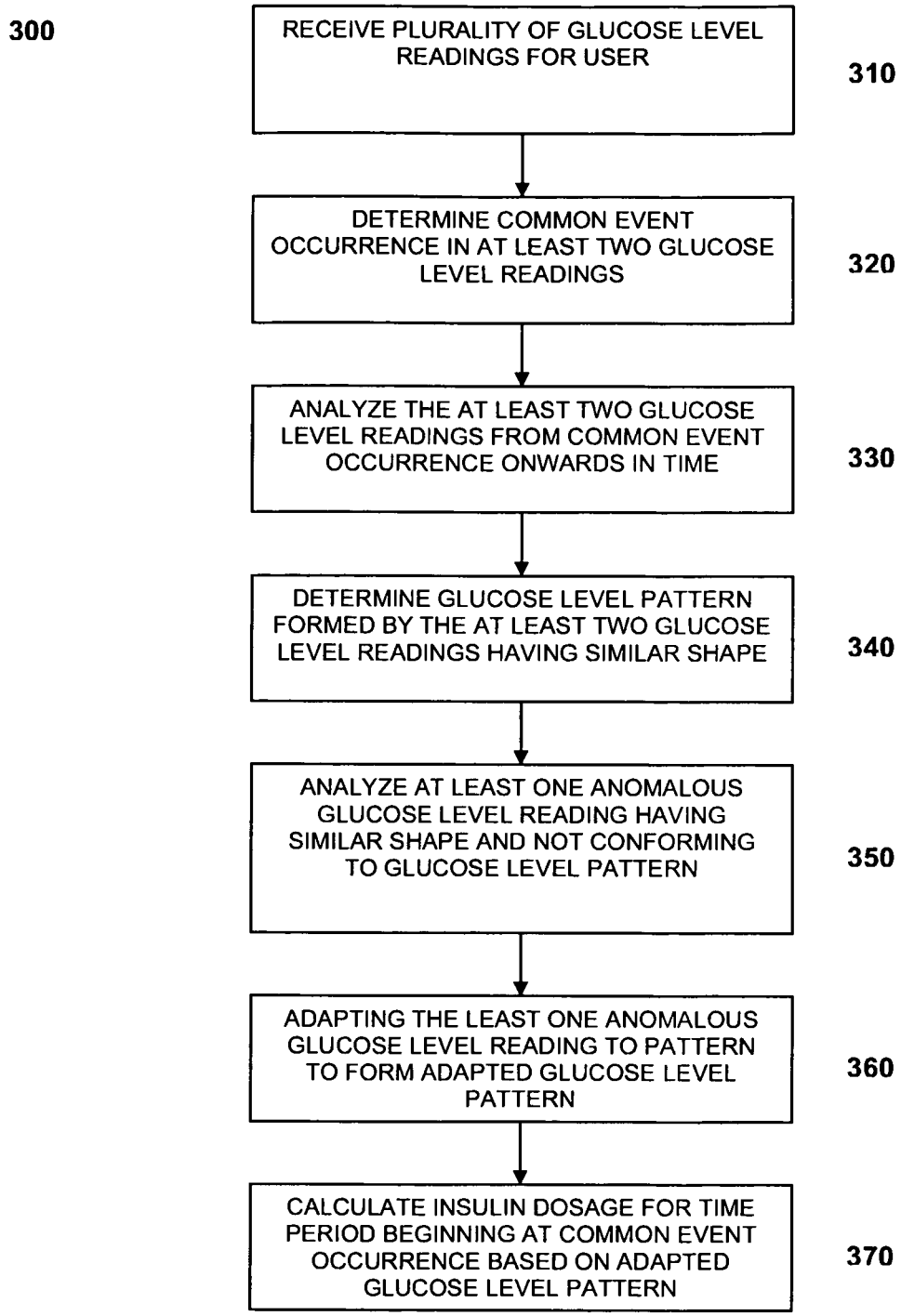
FIG. 3 illustrates a flowchart for applying pattern recognition and filtering algorithms for diabetes analysis according to embodiments of the present invention.

FIG. 3 illustrates a flowchart for applying pattern recognition and filtering algorithms for diabetes analysis according to embodiments of the present invention. According to embodiments of the present invention, a method of diabetes analysis includes, at step 310, receiving a plurality of glucose level readings for a user. The glucose level readings (e.g., daily 24-hour glucose level readings for a plurality of days as in FIG. 2A) may be obtained via a DDMS/MDMS system as discussed with respect to FIG. 1 above, or by any other suitable methods and means. According to embodiments of the present invention, the data used for analysis may exclude data from the most recent days. For example, if a user is learning a new behavior, then the most recent days may not generate the same patterns as previously, and data from a more consistent time in a user's life may generate more useful patterns for analysis and treatment planning. At step 320, a common event occurrence in at least two of the glucose level readings is determined. These common event occurrences may be used as reference/anchoring points in time (e.g., starting points, mid-points, end points) to analyze the glucose level readings amongst all of the readings relative to each common event occurrence, and trends and patterns may be perceived as to certain tendencies that may occur for a user relative to these specific event occurrences in that user's life (e.g., breakfast, lunch, dinner, watching the evening news, delivering a meal or correction bolus, etc.).

At step 330, the at least two glucose level readings from the common event occurrence onwards in time for a time period is analyzed to determine, at step 340, whether there is at least one glucose level pattern formed by the at least two glucose level readings having a similar shape. By analyzing the data, for example, in the representative charts illustrated in FIGS. 2B-2K, the DDMS/MDMS may determine that a pattern having a similar shape of two small successive dips followed by a large rise in glucose levels exist for several of the glucose level readings. This particular pattern of dips and rises is merely an illustrative example, and according to embodiments of the present invention, any other patterns and types of patterns may be analyzed.

At step 350, at least one anomalous glucose level reading having the similar shape and not conforming to the glucose level pattern is analyzed. For example, referring to FIGS. 2B-2J, glucose level reading lines 258, 268, 278, 288 appear to be anomalies such that they generally share the similar shape and slopes as with the remaining glucose level readings in their respective charts, but these anomalous lines do not conform to the pattern formed by the other glucose level readings in their respective charts. The at least one anomalous glucose level reading may be adapted to the pattern, at step 360, by the DDMS/MDMS to form an adapted glucose level pattern, for example, as illustrated in FIGS. 2C, 2E, 2G, 2I. According to embodiments of the present invention, at step 370, an insulin dosage for the time period beginning at the common event occurrence may be calculated based on the adapted glucose level pattern.

Figure 4:
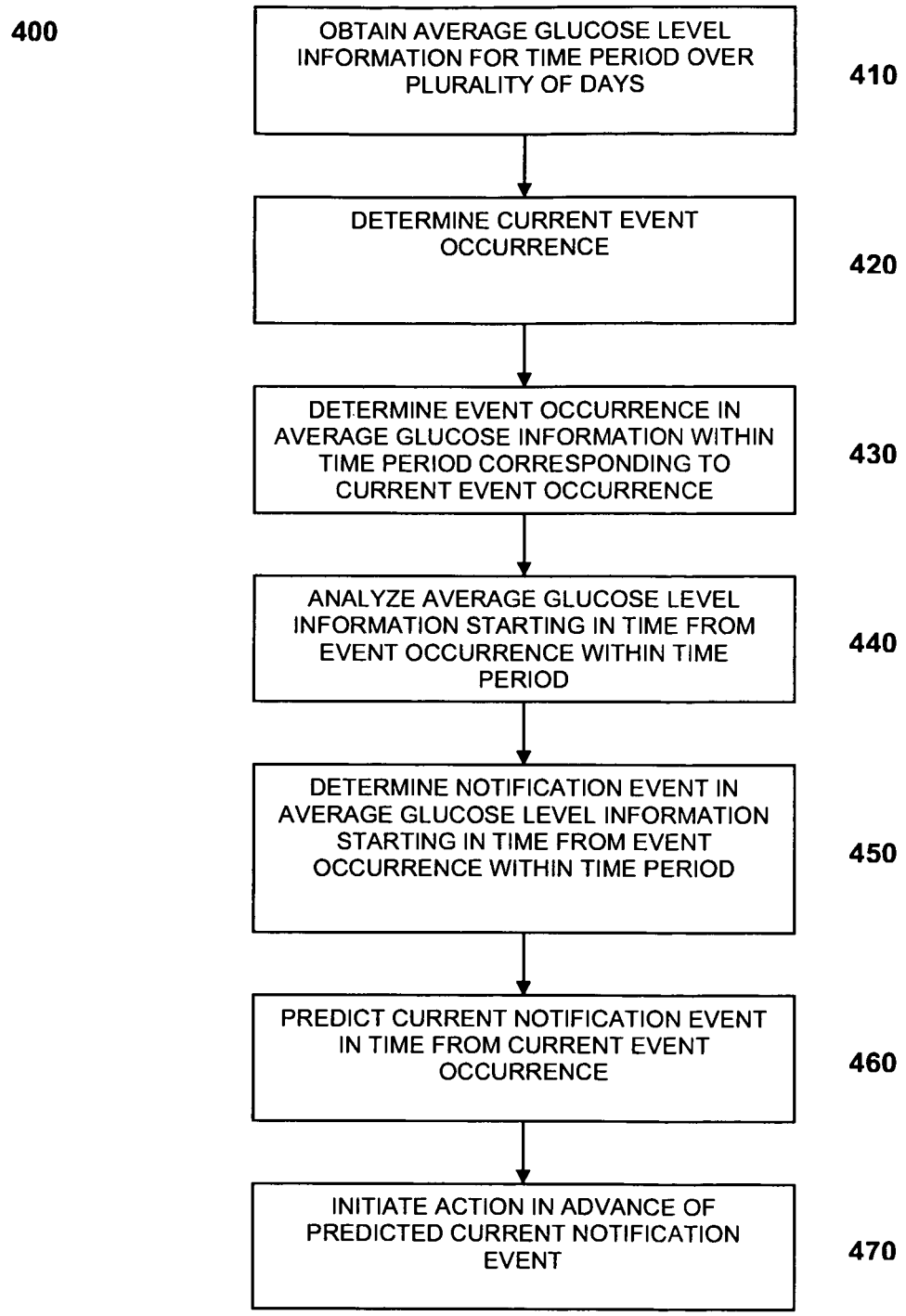
FIG. 4 illustrates a flowchart for diabetes analysis according to embodiments of the present invention.

FIG. 4 illustrates a flowchart for analysis of diabetes information according to embodiments of the present invention. According to one embodiment of the present invention, a method of analysis using time-shifted patterns of average glucose level information includes, at step 410, obtaining average glucose level information for a time period over a plurality of days. A chart, for example, like in FIG. 2A, of overlapping glucose level information for a period of days (e.g., 28-days in FIG. 2A) to obtain average glucose level information for a 24-hour time period may be utilized. Next, at step 420, a current event occurrence is determined (e.g., breakfast, lunch, or dinner, watching the morning/evening TV news, having afternoon tea, etc.).

Assuming that the user is about to have lunch (the current event occurrence), at step 430, an event occurrence (i.e., lunch at Noon shown at line 210 in FIG. 2A) in the average glucose level information within the time period corresponding to the selected current event occurrence (i.e., lunch now) is determined. The current event occurrence (lunch now) is at a different time of day than the event occurrence. For example, the user took lunch at Noon every day in the 28-day report of FIG. 2A, and the average glucose level information in FIG. 2A reflects that the user took lunch at Noon each day during this 28-day period. However, in the present example, the user was caught in a business meeting that ran long and the user is now taking lunch an hour later that usual, at 1 PM. Embodiments of the present invention are also applicable if the current event occurrence occurs earlier than the event occurrence in the average glucose level information (e.g., the user took lunch at 11:30 AM instead of Noon).

At step 440, the average glucose level information starting in time from the event occurrence (i.e., lunch at Noon shown at line 210 in FIG. 2A) within the time period is analyzed. That is, the average glucose level information pattern from the event occurrence onwards is analyzed to determine whether there is, at step 450, a notification event in the average glucose level information starting in time from the event occurrence within the time period. For example, the average glucose level information in FIG. 2A is analyzed to see whether there is a notification event (i.e., a significant, alarm, or any other event that may be of interest to the user, a medical professional, researcher, etc.). In the example illustrated in FIG. 2A, we note that there is a pattern in which the user's average glucose level tends to rise and peak shown at line 220 about three hours after the start of lunch at Noon shown at line 210, constituting a notification event in the present example.

Based on the time-shifted pattern according to embodiments of the present invention, at step 460, a current notification event in time from the current event occurrence (i.e., lunch now at 1 PM) is predicted based on a time span from the event occurrence (lunch at Noon shown at line 210 from report 200 in FIG. 2A) and the notification event (rise and peak shown at line 220 in FIG. 2A) from the average glucose level information in FIG. 2A. In the present example, the user took lunch at 1 PM instead of the usual Noon lunch time, and given that the 28-day average glucose level pattern in FIG. 2A shows a rise and peak at line 220 occurring three hours after the start of lunch at Noon shown at line 210, according to embodiments of the present invention, this pattern starting at lunch at Noon shown at line 210 onwards may be time-shifted an hour later to predict that a similar current notification event of a rise and peak three hours following the start of lunch would be approximately 4 PM. From this prediction, at step 470, an action may be initiated in advance of the predicted current notification event that is forecasted to occur around 4 PM, three hours after starting lunch at 1 PM.

Accordingly, in the present example as illustrated in FIG. 2A, the average glucose level pattern shows that a rise starts at 1 PM, an hour after the start of lunch at Noon shown at line 210. Therefore, if the user in this instance started lunch at 1 PM, an hour later than usual, an action may be taken to alert the user of a predicted rise that will start at approximately 2 PM, an hour after taking lunch. The user may be instructed to temporarily increase the basal rate for the next few hours or to deliver a bolus to minimize the rise and peak as predicted from the time-shifted average glucose level pattern (e.g., the "afternoon" pattern), or if so configured, to automatically increase the insulin delivery rate (basal or temporary) or administer a bolus, during this predicted rise and peak period so as to keep the user's glucose levels as stable as possible and within the desired glucose level range.

A pattern that may be time-shifted may constitute the entire 24-hour period of the average glucose levels, as illustrated in FIG. 2A, or any portion thereof. For example, the 24-hour period may be partitioned into three patterns for time shifting purposes, corresponding to three main meals per day (breakfast, lunch, and dinner), each pattern beginning at the start of an event occurrence (breakfast, lunch, or dinner) and ending right before the start of the next event occurrence. Referring to FIG. 2A, if we know that the user usually has breakfast at 6 AM shown at line 240, then one pattern may constitute the average glucose levels from 6 AM to Noon (the breakfast/morning pattern), and then a second pattern may constitute the average glucose levels from Noon (lunch time shown at line 210) to 7 PM (the lunch/afternoon pattern), and lastly a third pattern may constitute the average glucose levels from 7 PM (dinner time shown at line 230) to 6 AM the next day (the dinner/evening pattern). Each of these three patterns may be used for time-shifting purposes to predict potential notification events; a single 24-hour pattern or any portion thereof, divided into any number of patterns, corresponding to any suitable event occurrence, may be utilized according to embodiments of the present invention. Insulin dosage/delivery patterns may be programmed, e.g., in an insulin pump or any other suitable device, to match the representative patterns generated above, such that the user may be able to select, for example, a "breakfast", "lunch", or "dinner" insulin delivery pattern at the appropriate time or event to deliver insulin to keep the user's glucose levels as stable as possible and within the desired range.

Patterns and time lines are often helpful in linking causes to effects. Rates of change (e.g., what is the highest point we can reach before we need to make a correction) are often helpful in determining a significant or triggering event. Inappropriate alarm settings, for example, may lead to behaviors that may be detrimental to therapy. Inappropriate alarm settings may be ignored by the user, and then when a real critical alarm event occurs, the user may ignore this important alarm event as well (i.e., "crying wolf"). Therefore, making sure that the data is accurate is important in reducing the occurrence of inappropriate false alarms that may train "bad" behaviors in the user.

Factors that may influence the data quality used to develop a treatment plan may include: use of finger sticks to determine glucose levels, use of glucose sensors, use of accurate carbohydrate estimate counts, use of properly placed markers such as meal, activity, medication, stress, etc., and accurate insulin delivery. Most of these factors provide enough data in themselves that treatment plans based on these factors are generally reliable. Other factors that may influence the data quality and a user's adherence to the treatment plan may include: how often an infusion set is changed, how often calibration of the various medical devices are performed, common deceptions (e.g., overpriming an infusion pump), quality of the bolus calculator recommendations and overrides applied by the user. If a user is not following the bolus calculator recommendations, then a doctor may infer that the settings for the bolus calculator are not accurate and/or helpful, and may be prompted to reset them to be more accurate.

Various effects or conditions may result due to different treatment actions or causes, including hyperglycemia and hypoglycemia (both of which may influence pattern strength and pattern severity), and rising and falling glucose levels, including sharp spikes and drops (which may result from "unmarked" meals). Actions or causes for these varies conditions or effects applied in treatment may include: the basal (pattern) vs. bolus (impulse) settings, which in turn are influenced by the bolus impulses administered, use of carbohydrate ratios, a person's insulin sensitivity, the active insulin already administered to a person, as well as the time of day (e.g., late afternoon, evening, etc.), and whether or not a person is active or ill, under stress, etc. Delivery of a bolus resulting from a bolus calculator recommendation, suspension of delivery of insulin, or setting a temporary basal rate may also have effects on a person's glucose levels. Alarms may be tied to the occurrence of varies events, too.

If a database of "Bolus Type=Effect" information is available, some predictions may be made such that when a person encounters a particular event or pattern, based on the database information and recognizing the event or pattern occurring, a particular bolus type that can mitigate the undesired event or pattern may be recommended based on past data from the user or a plurality of users. Additionally, if the user exhibits a particular glucose level pattern following a particular event or activity, e.g., a meal, an 20-minute afternoon nap, a particular type of exercise, etc., we may adjust the user's basal rate (especially if we know the user's current insulin-on-board and glucose level) based on the observed patterns in advance of the user performing the particular activity, e.g., doing three sets of 15 pull-ups, running a mile on the treadmill at a 6.5 MPH pace, etc., to keep the user's glucose levels as stable as possible and within the desired range.

Other methods of managing therapy may include the use of a "virtual patient". A virtual patient is a digital model of an actual human patient on a computer to simulate different ways diabetes, or any other medical condition, affects the body, and how various treatments may potentially affect the virtual patient. Virtual patients may help cut the time and costs of development and testing of new treatment plans. For example, by knowing a patient's insulin sensitivity (everyone has different insulin sensitivities, and for Type I diabetics, e.g., they are often more sensitive in the late afternoons), certain predictions may be made and patterns from the virtual patient may be identified and tested to see if they are close to real life. Further description of a virtual patient software system may be found in U.S. Pat. App. Pub. No. 2006/0272652, published Dec. 7, 2006, to Stocker et al. and entitled "Virtual Patient Software System for Educating and Treating Individuals with Diabetes", which is herein incorporated by reference in its entirety.

Doctors often have access to data of multiple patients. By comparing the data of multiple patients in a doctor's patient pool, group patterns may be developed that may be helpful in treating particular patients. Similar patterns in multiple patients may help a doctor plan a course of treatment that may help another patient having such similar patterns. Data from multiple patients in a doctor's care may be utilized for virtual patient simulations, too, along with developing an "average patient" model as a point of reference.

Group patterns may be filtered by sex, age, pregnancy state, exercise type, body type, type of diabetes (Type I, Type II, gestational), treatment type (pump use, insulin type use, oral medication), etc. Another group may involve "panic" users, those who tend to over-deliver boluses upon a triggering or notification event. Accordingly, the infusion pump, controller/programmer, or any other suitable device may be configured such that when it recognizes a glucose level pattern occurring that has historically lead to a user over-delivering insulin, the infusion pump may warn the user in advance of this triggering event to not over-deliver a bolus. Additionally, the infusion pump, controller/programmer, or DDMS/MDMS, may automatically disable itself for a short period of time after the proper dosage has been delivered to prevent over-delivery by a panicked user. Group patterns also may be useful in assessing and identifying a "type" of patient, particularly helpful in establishing a starting point for a new patient.

"Distracted" users may forget to treat diabetes by skipping boluses, eating high sugar foods, forgetting to turn on the insulin pump after suspending insulin delivery during exercise, or forgetting to calibrate a sensor before bedtime (which may lead to the user being awakened during the night for a calibration). Patterns may be used to quickly identify that a bolus was missed or that a high sugar drink was consumed and warn the user to deliver a bolus before glucose levels reach severe hyperglycemia. Likewise, patterns may be used to identify early that exercise has stopped and the pump's bolus delivery must resume. Similarly, patterns may be used to identify habitual lapses in compliance and remind the user to perform a task when the user is awake and when it is convenient.

A user's exercise regime also should be considered when planning a course of treatment. An infusion pump or controller/programmer, for example, may include an accelerometer, heart rate monitor, respiratory monitor, etc., to deduce when a user may be exercising. Sometimes a user will remove a pump just before undergoing exercise, or set a temporary basal rate just before exercising to prevent a drop in glucose levels. Further descriptions of utilizing accelerometers in diabetes therapy may be found in U.S. Pat. App. Pub. No. 2008/0125701, published May 29, 2008, to Moberg et al. and is entitled, "Methods and Apparatuses for Detecting Medical Device Acceleration, Temperature, and Humidity Conditions", which is herein incorporated by reference in its entirety.

As with patterns of glucose levels, patterns of insulin delivery, e.g., basal patterns, also may be established corresponding to the glucose level patterns to keep the glucose levels within the desirable range throughout the day. Based on a glucose level pattern, an insulin delivery pattern may be established to anticipate and "match" rises and falls and keep the glucose levels within the desired range. Multiple patterns may be established for varies times throughout the day, too. For example, there may be an "after breakfast" pattern, an "after lunch" pattern, an "after dinner"/overnight pattern, etc. One pattern may be more useful to a user than another, and if a doctor sees that a user is using one pattern but not another, the doctor may deduce that the other unused pattern is not configured correctly and may further adjust this pattern to make it more effective to the user.

According to embodiments of the present invention, an after dinner/overnight pattern may be used to evaluate whether a user must take an action before bedtime. For example, if a user exercises earlier in the day, his/her body may demand nutrition to heal while sleeping, and the user's glucose levels may drop during the night to hypoglycemic levels. We may observe patterns of the glucose levels before bedtime and during the night, and if a hypoglycemic pattern is identified before going to bed, the user may take action to prevent low glucose levels, such as eating a snack before bedtime, eating a fatty snack so that digestion is postponed, reducing the basal insulin amount, changing the basal insulin profile, setting an alarm to get a snack later, etc.

The more accurate a user is at making an estimate of his/her carbohydrate intake, the more accurate the delivery of the correct amount of insulin required to keep a user's glucose levels stable and within the desired range. The Medtronic MiniMed BOLUS WIZARD™ calculator, for example, is a bolus estimator/calculator that assists a user in providing a recommended insulin bolus dosage for a meal based on the user's estimate of the amount of carbohydrates in a meal to be consumed. Further descriptions of a bolus calculator may be found in U.S. Pat. No. 6,554,798, issued Apr. 29, 2003, to Mann et al. and is entitled, "External Infusion Device with Remote Programming, Bolus Estimator and/or Vibrational Alarm Capabilities", and U.S. Pat. No. 7,204,823, issued Apr. 17, 2007, To Estes et al. and is entitled, "Medication Delivery System and Monitor", which are herein incorporated by reference in their entirety. Certain people are more accurate at estimating the amount of carbohydrates in a particular food or food type than others. For example, some people are better at estimating the carbohydrate amount in foods with generally high carbohydrate counts (e.g., potatoes) than those with the lower ones (e.g., eggs).

According to embodiments of the present invention, a bolus calculator may be calibrated ahead of time by the user to learn of the user's biases and tendencies to estimate high or low for certain (or all) foods (e.g., an apple, orange juice, pepperoni pizza, baked salmon, steamed rice, etc.) and food types (e.g., grains, vegetables, fruits, dairy products, meats, etc.), and then adjust the recommended insulin bolus dosage based on the user's biases and tendencies (if any). For example, the bolus calculator may be calibrated using a computer, such as the DDMS/MDMS discussed above with respect to FIG. 1, or the like, which may display a variety of different portions of foods with known true carbohydrate counts, and ask the user to provide his/her own estimates of the carbohydrate counts for the foods (and portions/amounts thereof) presented. By comparing the user's estimated carbohydrate count with the known true carbohydrate count for a variety of different foods, food types, food subtypes, etc., a calibration may be made to assist in providing more accurate insulin bolus dosage recommendations.

For example, it can be determined that the user estimates higher than true carbohydrate counts for pizza in general, while the user provides accurate estimates with meats and wheat-based foods in general, but the user underestimates the carbohydrate counts for sushi and fruits in general. Based on this calibration, the bolus calculator may adjust the insulin dosage recommendations to compensate for the user's biases in estimating high or low for particular foods and food types, and make little or no adjustments when the user is known to make accurate estimates for other foods and food types. Therefore, the bolus dosage recommendation is increased if the user's response to estimate the carbohydrate value for a representative food corresponding to a food to be consumed is lower than the true carbohydrate value for the representative food during calibration. Likewise, the bolus dosage recommendation is decreased if the user's response to estimate the carbohydrate value for a representative food corresponding to a food to be consumed is higher than the true carbohydrate value for the representative food during calibration. Any particular foods, food types, and food subtypes (e.g., for grains—wheat foods, rice foods, etc.) are suitable for calibration of the user's ability to estimate accurately carbohydrate counts for the various foods, food types, and food subtypes the user wishes to consume.

According to embodiments of the present invention, the bolus calculator may permit the user to select and calibrate with favorite foods or those foods that are commonly eaten by the user to obtain the most accurate and useable bolus dosage recommendations. For example, if the user hates or has severe allergies to shrimp foods, then, there is no need to calibrate with shrimp foods. The bolus calculator may also permit the user to designate an origin of the foods and calibrate accordingly, e.g., calibrate a pizza from California Pizza Kitchen vs. a pizza from Domino's vs. a frozen pizza from Costco. The bolus calculator may even permit the user to calibrate specific foods, e.g., a pepperoni and green pepper pizza (from Domino's) vs. a sausage and mushroom pizza (from Costco). Any combinations of the foods, food types, food subtypes, specific foods, and their origins, brands, etc. may be incorporated into the bolus calculator for calibration of the bolus calculator based on the user's ability to accurately estimate carbohydrate counts and adjust the bolus dosage recommendations based on those estimates.

Figure 5:
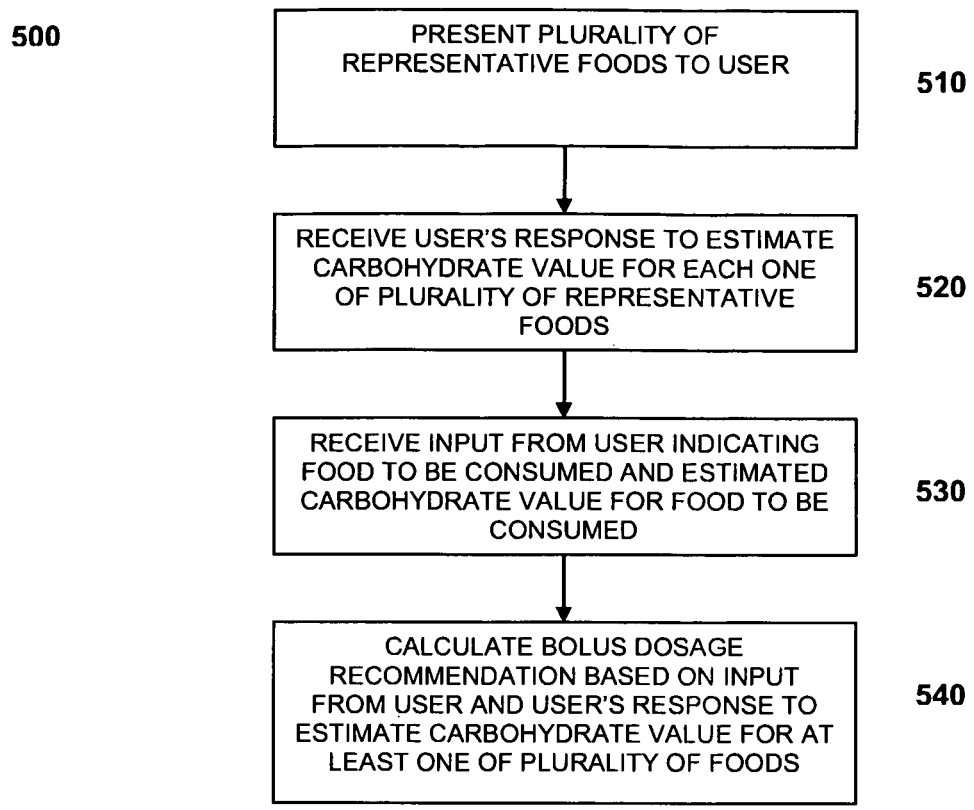
FIG. 5 illustrates a flowchart for providing bolus dosage recommendations for diabetics according to embodiments of the present invention.

FIG. 5 illustrates a flowchart for providing bolus dosage recommendations in diabetes therapy according to embodiments of the present invention. According to embodiments of the present invention, a method of calibrating and providing bolus dosage recommendations in diabetes therapy includes, at step 510, presenting a plurality of representative foods to a user. A spectrum of representative foods (especially those foods that a user is likely to consume) is selected and presented to the user that is reflective of the typical diet of the user. For example, these foods may be presented on a display of a computer or other suitable device, including but not limited to the DDMS/MDMS described above with respect to FIG. 1. The user is then prompted to estimate a carbohydrate value for each one of the plurality of representative foods presented to the user. The user may account for the portion (large, small, two vs. three egg omelet, etc.) of the representative foods presented to the user when estimating the carbohydrate value. Alternatively, the user may respond with "N/A", "SKIP", "REMOVE", or the like for those representative food(s) presented to the user that the user does not commonly eat or enjoy, to which the user has allergies, is not readily available where the user lives, etc.

At step 520, the responses from the user are received and stored by the computer or other suitable device. These responses are then used to calibrate a bolus calculator to determine whether the user has a tendency or bias to estimate high or low for particular foods, food types, food subtypes, etc. from their true carbohydrate value. Based on the estimates received from the user during calibration, the bolus calculator may make any adjustments or corrections in providing bolus dosage recommendations.

When the user is about to consume a food item, the user provides information to the bolus calculator indicating a food to be consumed and the user's estimated carbohydrate value for that food to be consumed. The bolus calculator, receiving the information regarding the food to be consumed at step 530, may be the computer that was used in the calibration, a separate device (e.g., a PDA, portable computer, mobile phone, etc.), or even integrated into the infusion pump or controller/programmer (that may receive calibration information from a computer used to conduct the calibration of the bolus calculator). The bolus calculator at step 540 calculates a bolus dosage recommendation based on the input received from the user regarding the food to be consumed (e.g., food, food type, food subtype, estimated carbohydrate count, portion, origin, brand, etc.) and the user's response to estimate the carbohydrate value for at least one of the plurality of representative foods during calibration in steps 510 and 520.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

The invention claimed is:

1. A method of diabetes analysis, comprising:
   receiving, using a processor and a glucose sensor, a plurality of glucose level readings over a plurality of days for a user, each of the plurality of glucose level readings having multiple glucose level measurements for one of the plurality of days;
   determining, using the processor, a common event occurrence in at least two of the glucose level readings;
   analyzing, using the processor, the at least two glucose level readings from the common event occurrence onwards in time for a time period;
   identifying, using the processor, a glucose level pattern formed by the at least two glucose level readings having a similar shape;
   analyzing, using the processor, an anomalous glucose level reading not conforming to the glucose level pattern to determine whether the anomalous glucose level reading has the similar shape;
   adjusting, using the processor, the anomalous glucose level reading to adapt to the glucose level pattern to form an adapted glucose level pattern if the anomalous glucose level reading has the similar shape;
   filtering out, using the processor, the anomalous glucose level reading if the anomalous glucose level reading does not have the similar shape;
   calculating, using the processor, an insulin dosage for the time period beginning at the common event occurrence based on the adapted glucose level pattern; and
   initiating an action, wherein the action includes at least one of recommending the calculated dosage and automatically delivering the calculated insulin dosage,
   wherein the method is implemented on a portable medical system.

2. The method of claim 1, wherein the common event occurrence is selected from the group consisting of: breakfast, lunch, dinner, a meal bolus, a correction bolus, and a bedtime.

3. The method of claim 1, wherein the insulin dosage is for a basal insulin dosage.

4. The method of claim 1, wherein the at least one anomalous glucose level reading having the similar shape has at least one of: a greater or lesser magnitude, and a higher or lower basal glucose level than the at least two glucose level readings forming the glucose level pattern.

5. The method of claim 1, wherein adjusting, using the processor, the anomalous glucose level reading to adapt to the glucose level pattern if the anomalous glucose level reading has the similar shape includes at least one of: shifting the anomalous glucose level reading in time compared to the at least two glucose level readings forming the glucose level pattern, normalizing a magnitude of the anomalous glucose level reading toward a target range of glucose level measurements, compressing or stretching the anomalous glucose level reading in time compared to the at least two glucose level readings forming the glucose level pattern, and shifting the anomalous glucose level reading toward the target range of glucose level measurements.

6. The method of claim 1, wherein the plurality of glucose level readings for the user excludes readings from at least one recent day.

7. The method of claim 1, wherein the plurality of glucose level readings are selected only from days that the user has a periodic or transient condition.

8. An article of manufacture containing code for diabetes analysis, comprising a computer-usable medium including at least one embedded computer program that is capable of causing at least one computer to perform:
    receiving a plurality of glucose level readings over a plurality of days for a user from a glucose sensor, each of the plurality of glucose level readings having multiple glucose level measurements for one of the plurality of days;
    determining a common event occurrence in at least two of the glucose level readings;
    analyzing the at least two glucose level readings from the common event occurrence onwards in time for a time period;
    identifying a glucose level pattern formed by the at least two glucose level readings having a similar shape;
    analyzing an anomalous glucose level reading not conforming to the glucose level pattern to determine whether the anomalous glucose level reading has the similar shape;
    adjusting the anomalous glucose level reading to adapt to the glucose level pattern to form an adapted glucose level pattern if the anomalous glucose level reading has the similar shape;
    filtering out the anomalous glucose level reading if the anomalous glucose level reading does not have the similar shape;
    calculating an insulin dosage for the period beginning at the common event occurrence based on the adapted glucose level pattern; and
    initiating an action, wherein the action includes at least one of recommending the calculated insulin dosage and automatically delivering the calculated insulin dosage,
    wherein the article of manufacture is a portable medical system.

9. The article of claim 8, wherein the common event occurrence is selected from the group consisting of: breakfast, lunch, dinner, a meal bolus, a correction bolus, and a bedtime.

10. The article of claim 8, wherein the insulin dosage is for a basal insulin dosage.

11. The article of claim 8, wherein the anomalous glucose level reading having the similar shape has at least one of: a greater or lesser magnitude, and a higher or lower basal glucose level than the at least two glucose level readings forming the glucose level pattern.

12. The article of claim 8, wherein adjusting the anomalous glucose level reading to adapt to the glucose level pattern if the anomalous glucose reading has the similar shape includes at least one of: shifting the anomalous glucose level reading in time compared to the at least two glucose level readings forming the glucose level pattern, normalizing a magnitude of the anomalous glucose level reading toward a target range of glucose level measurements, compressing or stretching the anomalous glucose level reading in time compared to the at least two glucose level readings forming the glucose level pattern, and shifting the anomalous glucose level reading toward the target range of glucose level measurements.

13. The article of claim 8, wherein the plurality of glucose level readings for the user excludes readings from at least one recent day.

14. The article of claim 8, wherein the plurality of glucose level readings are selected only from days that the user has a periodic or transient condition.

* * * * *